(12) United States Patent
Yang

(10) Patent No.: US 6,944,259 B2
(45) Date of Patent: Sep. 13, 2005

(54) VERSATILE CONE-BEAM IMAGING APPARATUS AND METHOD

(75) Inventor: Xiaochun Yang, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 180 days.

(21) Appl. No.: 10/256,727

(22) Filed: Sep. 26, 2002

(65) Prior Publication Data

US 2003/0072406 A1 Apr. 17, 2003

Related U.S. Application Data

(60) Provisional application No. 60/325,055, filed on Sep. 26, 2001.

(51) Int. Cl.[7] .................................................. A61B 6/03
(52) U.S. Cl. ................................. 378/15; 378/4; 378/8; 378/901
(58) Field of Search ........................... 378/15, 8, 4, 901

(56) References Cited

U.S. PATENT DOCUMENTS

| | | |
|---|---|---|
| 5,592,523 A | 1/1997 | Tuy et al. |
| 5,625,660 A | 4/1997 | Tuy |
| 5,805,659 A | 9/1998 | Tam |
| 5,926,521 A | 7/1999 | Tam |
| 5,933,517 A | 8/1999 | Grangeat et al. |
| 5,999,587 A | 12/1999 | Ning et al. |
| 6,219,441 B1 | 4/2001 | Hu |
| 6,275,561 B1 | 8/2001 | Danielsson |
| 6,285,733 B1 | 9/2001 | Proksa et al. |
| 6,292,525 B1 | 9/2001 | Tam |
| 6,411,670 B1 | 6/2002 | Besson |
| 6,574,299 B1 | 6/2003 | Katsevich ................ 378/14 |
| 6,627,893 B1 * | 9/2003 | Zeng et al. ............ 250/363.04 |

FOREIGN PATENT DOCUMENTS

| | | |
|---|---|---|
| EP | 0292402 | 11/1988 |
| WO | WO 99/01066 | 1/1999 |
| WO | WO 01/06931 | 2/2001 |
| WO | WO 01/60236 | 8/2001 |

OTHER PUBLICATIONS

International Search Report for PCT US 02/30794, mailed Feb. 13, 2003.
Tang and Ning (2001) "A cone beam filtered backprojection (CB–FBP) reconstruction algorithm for a circle–plus–two–arc orbit" Med. Phys. 28(6):1042–1055.

* cited by examiner

Primary Examiner—David V. Bruce
Assistant Examiner—Elizabeth Gemmell
(74) Attorney, Agent, or Firm—Robert J. Sayre; Mintz, Levin, Cohn, Ferris, Glovsky and Popeo, P.C.

(57) ABSTRACT

A three-dimensional image of an object scanned with a plurality of cone-beam projections from a number of source positions is reconstructed using a method wherein intermediate transform functions are obtained from two-dimensional images of radiation attenuation in the scanned object. The intermediate transform functions are then filtered over the two-dimensional attenuation images using a moving-frame technique. The second-order radial derivative of the Radon transform can then be backprojected to generate an intermediate, locally-reconstructed, three-dimensional image. After repetition of this process, the plurality of intermediate, locally reconstructed, three-dimensional images are summed to obtain an ultimate, reconstructed, three-dimensional image of the object.

22 Claims, 11 Drawing Sheets

VERSATILE CONE-BEAM IMAGING APPARATUS AND METHOD

RELATED APPLICATION

This application claims priority to provisional patent application, U.S. Ser. No. 60/325,055, filed Sep. 26, 2002, the entire teachings of which are incorporated herein by reference.

BACKGROUND

Cone-beam computerized tomography (CT) reconstructs the density function of a three-dimensional object from a set of cone-beam projections. Such a system uses an area detector to receive rays emitted from an X-ray point source and attenuated by partial absorption in the object that they pass through. As in traditional (i.e., planar) CT, the source 10 and the detector 14 are placed on opposite sides of the object 12 being scanned (see FIG. 1). Rays contributing to an image on the detector surface form a cone with the X-ray source 10 at the apex. From the X-ray radiance value recorded at a point on the area detector 14, one can compute the integral of attenuation along the ray from the X-ray source 10 to the given point on the detector 14.

As the source-detector 10/14 pair undergoes a simultaneous rotation and translation around the object 12, a plurality of two-dimensional cone-beam images projected from various source positions can be acquired and used to reconstruct the distribution of absorption inside the three-dimensional object 12.

Compared to the traditional slice-at-a-time tomographic machine, the cone-beam CT offers faster scans, higher patient throughput, significant reduction in X-ray dosage, and isotropic resolution. It has a great potential to be applied to a wide range of medical and industrial applications.

Radon's 1917 inversion formula (Johann Radon "Über die Bestimmung von Funktionen durch ihre Integralwerte längs gewisser Mannigfaltigkeiten," *Ber. Verh. Sächs. Akad. Wiss. Leipzig. Math. Nat. Kl.*, Vol. 69, pp. 262–277, 1917) plays an important role in understanding the cone-beam reconstruction problem. The building blocks of the three-dimensional Radon inversion formula are planar integrals. We can write a plane in $R^3$ as $$L_{l,\beta} := \{x \in R^n | x \cdot \beta = l, l \geq 0, \beta \in S^{n-1}\}, \quad (1)$$

where $\beta$ is the unit normal of the plane and l is the perpendicular distance of the plane from the origin. The Radon transform of a function f on $R^3$ is defined as the set of integrals of $f$ over all the planes in $R^3$ which can be expressed as a function of two parameters (l and $\beta$):

$$f(x) = -\frac{1}{8\pi^2} \int_{S^2} \frac{\partial^2 Rf(l,\beta)}{\partial l^2}\bigg|_{l=x\cdot\beta} d\beta, x \in \Omega, \quad (3)$$

The Radon formula is given by:

$$Rf(l, \beta) := \int_{x \in \{x | x \cdot \beta = l\}} f(x) dx. \quad (2)$$

in which, $S^2$ denotes the two-dimensional unit sphere in $R^3$ and $\Omega$ denotes the support of $f$. The integral in Eqn. (3) over $S^2$ is the backprojection operator; it integrates over all the planes passing through x. The integration sphere is therefore called the backprojection sphere with its center at x, denoted by $S_x^2$ (x is considered as an index). It is clear that the points on $S_x^2$ represent the unit normals of all the planes through x.

To recover the function value at point x, $R''f(l,\beta)$ is obtained on all or almost all planes passing through x. In cone-beam reconstruction, however, planar integrals are not available from the cone-beam data because rays diverge from the point source inside each projection. Hence, the Radon formula (Eqn. (3)) is not immediately employed.

The first cone-beam inversion formula for real-valued functions is given by Tuy in 1983; this formula was a Fourier-based method (Heang K. Tuy "An Inversion Formula for Cone-Beam Reconstruction," *SIAM J. Appl. Math*, Vol. 43, 1983, pp. 546–552). Smith's paper in 1985 established connections between the cone-beam data and the second-order radial derivative of the Radon transform, R" f(Bruce D. Smith "Image Reconstruction from Cone-Beam Projections: Necessary and Sufficient Conditions and Reconstruction Methods," *IEEE Trans. Med. Imag.*, Vol. 4, 1985, pp. 14–25). The most important contribution in these early derivations is a clear understanding of the data sufficiency condition for an exact reconstruction, that is, almost all planes passing by the support of the object shall intersect with the source orbit.

The next significant breakthrough came with the discovery of the Fundamental Relation by Grangeat (Pierre Grangeat "Mathematical Framework of Cone-Beam 3D Reconstruction via the First Derivative of the Radon Transform," *Mathematical methods in tomography, Lecture notes in mathematics* 1497, 1991, pp.66–97. The Fundamental Relation relates the cone-beam data on a slice of fan-beams inside each cone-beam projection to the first-order radial derivative of the Radon transform, R'f. R'f serves as an implicit link between the cone-beam data and R" f. The second-order radial derivative of the Radon transform is needed in order to use Eqn. (3); R" f is then backprojected to recover f.

Though substantial progress has been made during the last two decades, the solutions for exact cone-beam reconstruction are still not fully satisfying. In many of the reconstruction methods that have been developed, the backprojection-differentiation operation inherited from the Radon formula appears ad hoc and is the most time-consuming step in the reconstruction.

The well-known filtered backprojection (FBP) cone-beam reconstruction technique, which is widely used in industry, is given by Feldkamp (FDK) et al. for circular source orbits (L. A. Feldkamp, L. C. David and J. W. Kress "Practical Cone-Beam Algorithm," *J. Opt. Soc. Am. A.*, Vol. 1, No. 6, 1984, pp. 612–619). In such a case, data from cone-beams with narrow angles is treated in an approximate way using extensions of two-dimensional fan-beam methods. The FDK algorithm is easy to implement; however, it only provides reasonably good reconstruction near the mid-plane and cannot be used for wide cone angles. Hence, alternative reconstruction methods and the embodying imaging apparatus are still being sought, particularly for the large-detector cone-beam system since it has become a reality.

In designing a dedicated cone-beam imaging system, finding a proper source orbit is a challenge. The selection of a good source orbit not only depends on the dimension of the object under investigation, but also depends on the geometric measurements such as the allowed source-to-object and detector-to-object separation. An important condition for accurate reconstruction is the data sufficiency condition. Another desirable feature of the selected source orbit is symmetry.

Among various source orbits that have been proposed, sinusoidal trajectory and helical trajectory meet both conditions. Though advantageous in their sampling performance, reconstruction procedure using these two scan paths have yet to achieve the desired efficiency. The principal difficulty encountered in the reconstruction is caused by the sophisticated mapping from the local projection geometry to the Radon space geometry characteristic to many non-planar source orbits.

Other approaches use two orthogonal planar trajectories such as circle-plus-circle, circle-plus-line and circle-plus-arc to fulfill the data sufficiency condition. Although the hybrid methods combine cone-beam data from two simpler scanning processes, they have two major disadvantages. First, the discontinuity in the mechanical movement makes them less attractive in practice. Second, sampling in the Radon space where the backprojection takes place is not balanced under these hybrid scanning geometries; this limits the reconstruction accuracy.

SUMMARY

A novel algorithmic paradigm for three-dimensional image reconstruction from cone-beam projections is disclosed, wherein a new class of algorithms, referred to as moving frame reconstruction (MFR) algorithms, is introduced. MFR algorithms have the ability to invert a set of cone-beam images progressively and simultaneously in conjunction with the X-ray scanning process.

In terms of the reconstruction procedure, the most complex and expensive computation in cone-beam imaging lies in the backprojection-differentiation operation. Described herein is a technique that enables systematic implementation of the backprojection-differentiation operation and which can be described by the following procedures.

A radiation source is initially positioned on a predetermined scan path. The source generates projection of cone-beam radiation from a common focal point. The projection, which comprises a plurality of projection "rays," passes from the source through the object, and the object attenuates the cone-beam projection as it passes therethrough. The radiation intensity of the attenuated cone-beam image is then detected on an area detector, and a two-dimensional attenuation image of the cone-beam projection is obtained from the detected radiation intensities.

From each two-dimensional attenuation image, an intermediate transform function is obtained on a set of planes passing through the focal point. The source is then repositioned and these steps are repeated.

After two or more repetitions of the above steps, the intermediate transform functions acquired from consecutive attenuation images are filtered using a moving-frame technique to obtain the second-order radial derivative of the Radon transform. The second-order radial derivative of the Radon transform is then backprojected in two-dimensional space along each projection ray to generate an intermediate, locally reconstructed, three-dimensional image with constant values assigned along each projection ray. The procedure comprising repositioning the source; obtaining (a) a two-dimensional attenuation image, (b) an intermediate transform function, and (c) a second-order radial derivative of the Radon transform; and then backprojecting that second-order radial derivative of the Radon transform is then repeated at least once.

Finally, the plurality of intermediate, locally reconstructed, three-dimensional images are summed to obtain an ultimate, reconstructed, three-dimensional image of the object.

In one embodiment, the method for performing the above-described steps of backprojecting the second-order radial derivative and summing the plurality of intermediate, locally reconstructed, three-dimensional images can be expressed as the following decomposed Radon formula:

$$f(x) = -\frac{1}{8\pi^2} \int_\Lambda \left\{ \int_{\beta \in \{x - \Phi(\lambda)\}^\perp, \beta \in S^2} R'' f(\Phi(\lambda) \cdot \beta, \beta) \frac{|\Phi'(\lambda) \cdot \beta|}{M(\lambda, \beta)} d\beta \right\} d\lambda, \quad (4)$$

where $\Phi(\lambda)$ is a complete path and is analytic, which means infinitely differentiable. $M(\lambda, \beta)$ is the number of times that a plane passing by $(\Phi)(\lambda)$ and having unit normal intersects with the source orbit. The described plane can be written as $L_{l,\beta}$, where $l = \Phi(\lambda) \cdot \beta$. Hence the function $M(\lambda, \beta)$ is also considered as a function of l and $\beta$; without confusion, we can write it as $M(l, \beta)$, and it is referred to as the redundancy function.

The above mathematical formulism serves two prevailing geometric constraints underlying most of the cone-beam tomographic systems.

First, within each cone-beam projection, all the planes passing through a particular projection line have normals perpendicular to the same projection ray. As a result, backprojection orientation can be constrained onto a unit circle. This reduction of the backprojection from three-dimensional space to two-dimensional space brings great efficiency to the reconstruction method.

Second, as a radiation source traverses along the source orbit, each backprojection orientation undergoes a rigid rotation that can be described by a moving basis (e.g., determined by the local properties of the source orbit). The moving basis serves as a coordinate transform from the local projection frame to the global coordinates in the Radon space. As long as the source orbit satisfies the data sufficiency condition, one can succeed in decomposing the three-dimensional backprojection into a series of two-dimensional backprojections in accordance with the scanning geometry.

The source trajectory can be stored as software code in a computer-readable medium coupled with a computer processor. The processor, in turn is coupled with mechanical apparatus for moving the source along the source trajectory, and the processor following the instructions of the code so directs the source along the source trajectory and also directs the detector along a corollary trajectory. Alternatively, the code directs the rotation of the source to generate a similar relative displacement to the source and detector. Intensity values from the detector are communicated to computer-readable memory, where they are stored in digital form. Additional software code processes the intensity values in accordance with the algorithms described above to obtain the ultimate, reconstructed, three-dimensional image of the object.

Further, the above technique can be used with a wide selection of source orbits as well as variable source-detector configurations.

The new procedure allows simple and systematic approach to cone-beam tomographic reconstructions in general. A number of different source-detector configurations and orientations, as well as a large family of scanning orbits satisfying the so-called data sufficiency condition can be successfully treated in a unified mathematical framework with greater ease, simplicity and improved efficiency. The procedure is immediately suited to the cone-beam systems equipped with large area detectors, in which, the scanned object is positioned completely inside the field of view, and there is no data truncation.

Moreover, source orbits disclosed herein offer better sampling performance in the Radon space and consequently better image qualities in the reconstruction. A new family of source orbits disclosed herein is the biquardatic source curve. The parameters of the biquadratic source curve can be tuned in accordance with the dimension of the scanned object. Another benefit of using the biquadratic curve is that it has at most four intersections with a plane in the three-dimensional space. We are able to give an analytic procedure for deciding the number of intersections between a specified source orbit and an arbitrary plane in the three-dimensional space; the result is used to determine the weights of each plane passing by a particular source point along the source orbit.

Figure 1:
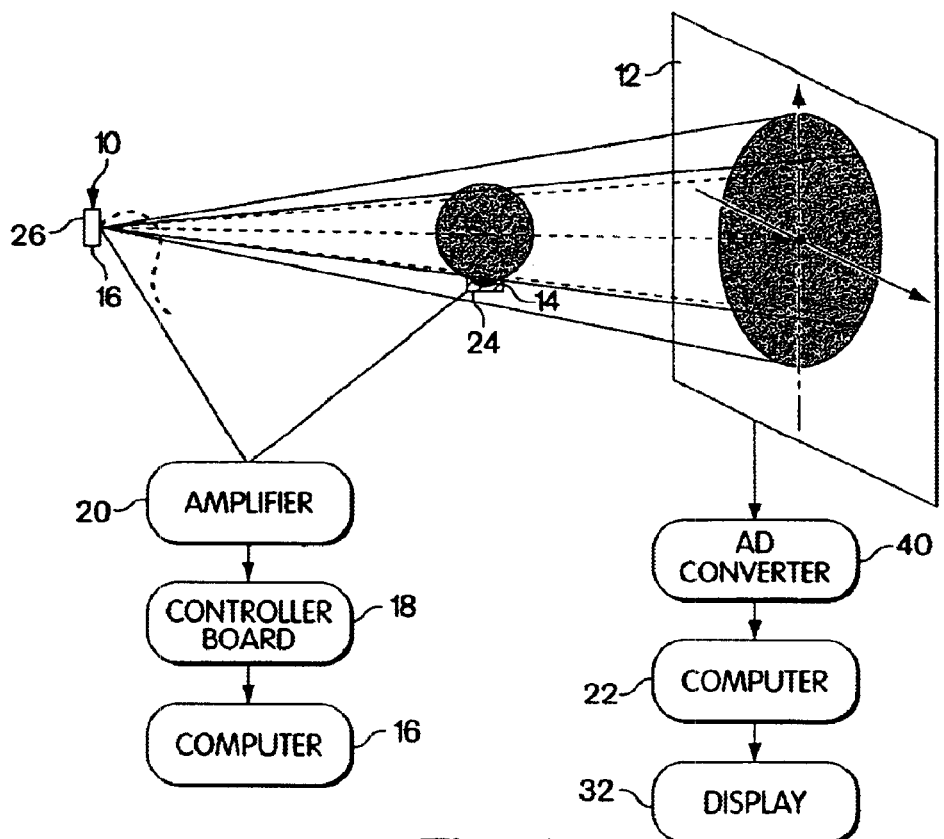
FIG. 1 illustrates a typical cone-beam imaging system with a radiation source and a 2D area detector rotating around the object being scanned.

The foregoing will be more apparent from the following, more-particular description. In the drawings, like reference characters refer to the same or similar parts throughout the different views. The drawings are not necessarily to scale, emphasis instead being placed upon illustrating particular principles, discussed below.

DETAILED DESCRIPTION

Figure 2:
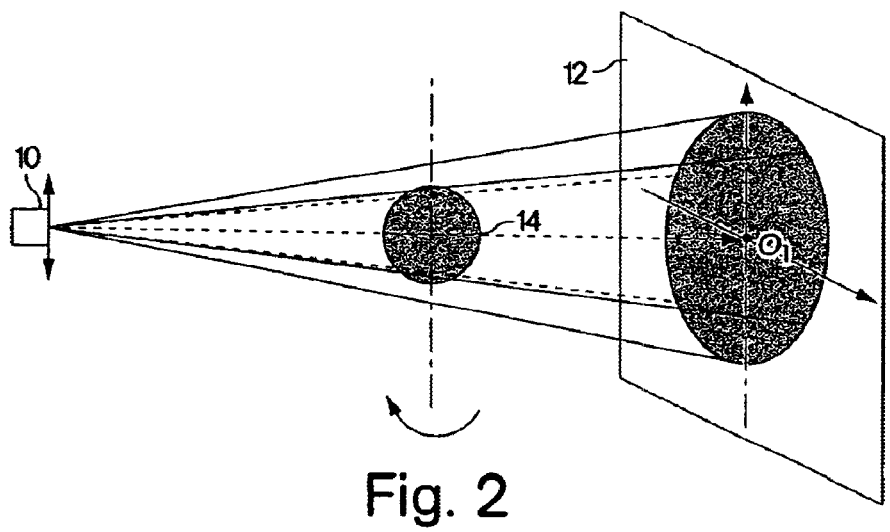
FIG. 2 provides a schematic illustration of a cone-beam imaging apparatus.

FIG. 2 illustrates a suitable apparatus for generating, detecting a plurality of X-ray cone-beam projections as well as recovering the three-dimensional attenuation map inside the object being scanned from the collected cone-beam projection measurement. Specifically, the physical hardware of a cone-beam imaging system comprises a radiation source 10 with a cone-beam collimator, a two-dimensional area detector 12 that receives the attenuated rays emitting from a point source and passing by the object, two motors 14 and 16, which are accountable for the relative movement between the source-detector system and the object, an analog-to-digital converter 40 that converts the detected cone-beam signals by the area detector into a digital format that enters the computer system 22 as input, and the computer system 22, which stores, processes the converted cone-beam data to reconstruct the attenuation distribution inside the object. The output of the reconstruction is a three-dimensional array that can be recorded in a readable media and displayed by an imaging or graphical display engine.

More specifically, the radiation source and the two-dimensional detector are placed on opposed sides of the object. A cone-beam projection comprises a plurality of projection rays connecting the radiation source and a plurality of detector elements on the detector surface. The plurality of projection rays thus form a cone with the focal point at the source point. The relative position of the source and detector are fixed during the scanning process. Whereas, the relative position of the source-detector pair and the object is controlled by the motors attached to the object support 24 and the source-detector support 26. Various mechanism for rotating the radiation source and the detector around the object are known in the art. For example, the object can be secured on a rotational turntable driven by a motor and the source and detector can be mounted on a pair of parallel slides whose synchronized translation is under the control of another motor. Alternatively, as in a medical CT scan, the radiation source and the detector can be mounted on a cylindrical gantry that rotates, and the object undergoes a simultaneous translation at a constant speed in the direction orthogonal to the rotational gantry. In both cases, the radiation source and the detector seem to travel along a smooth space curve while remaining at a fixed position relative to one another. This curve followed by the radiation source relative to the object being scanned is called the source orbit or the scan path.

Furthermore, the motors are driven by a controller board 18 which is capable of receiving the signals from a computer 16 and generating the commands that set the motors into a prescribed, synchronized rotation and translation. The output of the controller is amplified by the amplifier 20 so that the motor gets the required power for the motion. The imaging display engine 32 is capable of displaying two-dimensional images of the reconstructed attenuation map on an arbitrary cross-section, or processing the reconstructed three-dimensional array using a rendering algorithm that yields a three-dimensional anatomical representation of the object that can be viewed from various angles on a computer screen.

A basic setup for the cone-beam imaging apparatus is to establish the source orbit. Assume that the source orbit is parameterized by $\Phi(\lambda)=(\phi_1(\lambda), \phi_2(\lambda), \phi_3(\lambda))$, with $\lambda \in \Lambda$ being the parameter. Assume also that the source orbit resides outside the convex support of the object, denoted by $\Omega$. A preferred source orbit not only would satisfy the data sufficiency condition, but also would produce considerably even-sampled Radon space, which is defined as the space of all the planes passing by the object.

The data sufficiency condition is imposed to ensure that the collected cone-beam data, after an integral transform, can fill the entire Radon space. A source orbit that satisfies this condition is called a complete source orbit or a complete scan path.

To sample the Radon space uniformly means to produce relatively even-sampled backprojection sphere everywhere in the object space. The second goal is much more difficult to achieve. The size and the shape of the inspected object are important factors in selecting the source orbit; e.g., the optimal source orbit for round and elongated objects shall be different because they exhibit different kind of symmetries. Besides, the separation distance between the X-ray spot and the detector plane as well as the size of the area detector are also important constraints to be considered and accordingly to be compromised when choosing a suitable source orbit.

In one embodiment, the source orbit is controlled by mechanically independent rotational and linear motion. Assume that the rotational axis passes through the center of the object, which is shown in FIG. 2 as a vertical line. The first and second component of the source orbit is therefore on a circle, e.g., $\phi_1(\lambda)=R\cos(\lambda)$, $\phi_2(\lambda)=R\sin(\lambda)$ with $\lambda \in [0, 2\pi]$ and R the distance between the source and the rotational axis (this distance is fixed). We assume that the linear translation of the source in the z-dimension relative to the object has the following parametric form:

$$\phi_3(\lambda) = a^2\cos^2\lambda + b^2\sin^2\lambda - \frac{a^2+b^2}{2}. \tag{5}$$

Without loss of generality, we can assume that a>b. Note that $a^2-b^2$ determines the amplitude of the orbit and the ratio $(a^2-b^2)/R$ affects its elongation (See FIG. 3). The curve thus defined can be considered as the intersection of a cylinder and a parabola. They are both quadratic surfaces, so the intersecting curve is called biquadratic.

The number of intersections of a plane with a biquadratic curve is either 0, 1, 2, 3, or 4. Given a plane $L_{l,\beta}$, let OC be the line through the origin and perpendicular to the plane. OC intersects the plane at point $l\beta$. At the intersection $\Phi(\lambda)$, where the plane meets the curve, the following identity holds:

$$\beta \cdot (l\beta - \Phi(\lambda)) = 0. \tag{6}$$

It simplifies to $l = \beta \cdot \Phi(\lambda)$. Hence, $$\beta_1\cos\lambda + \beta_2\sin\lambda + \beta_3(a^2-b^2)\cos^2\lambda - l - \frac{a^2+b^2}{2} + \beta_3 b^2 = 0, \tag{7}$$

Where $\beta_1$, $\beta_2$ and $\beta_3$ are the three components of $\beta$. Letting $x=\cos\lambda (x\in[-1, 1])$, produces $$\beta_1 x + \beta_2\sqrt{(1-x^2)} + \beta_3(a^2-b^2)x^2 - l - \frac{a^2+b^2}{2} + \beta_3 b^2 = 0. \tag{8}$$

The above equation can be rearranged into a quartic equation (fourth order polynomial equation), for which, analytical solutions exist. Since the solutions are given explicitly, we can check if each real root is within [−1, 1]. If it is, then this root corresponds to an intersection point. One can write a simple program to find the number of intersections using the analytical formula for the roots of the quartic equation.

Figure 4:
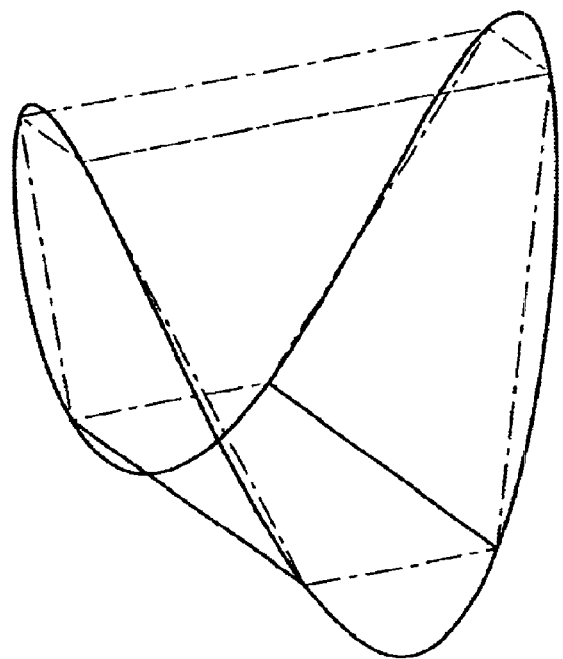
FIG. 4 provides a visualization of the convexification of the biquadratic source orbit.

The biquadratic curve paramaterized above is highly symmetric. In addition, its shape can be adjusted by the parameters R, a and b according to the dimension of the given problem so to meet the data sufficiency condition. In order for every plane passing through the object intersects with the source orbit, the object must be inside the convex hull of the source orbit. Let two horizontal planes cut through the source orbit near the bottom and the top of the curve | the eight intersections form a trapezoid as shown in FIG. 4. The object is completely inside the convex hull of the source orbit if the object is entirely inside the trapezoid.

Thus we can derive the condition for the parameterized biquadratic curve $\Phi(\lambda)$ being a complete scan path. Assume that the object center is at the origin. Also assume that it has a square base with width w and height h. Then $$a^2 - b^2 > h \ \& \ \sqrt{1-\left(1-\frac{h}{(a^2-b^2)R^2}\right)^2} > w \tag{9}$$

guaranties that $\Phi(\lambda)$ is a complete scan path. The above condition can be met by incorporating either $a^2-b^2$ or $R^2$.

One may use any source orbit that is both a complete scan path and analytic, which means that the curve is infinitely differentiable almost everywhere with exception allowed for a zero measure set. In real life most of the curves we encounter are analytic curves. A more general embodiment may encompass any curve that is everywhere differentiable except at a finite number of points, such as a circular trajectory which is not a complete source orbit but which can generate an approximate reconstruction from the incomplete cone-beam data.

Other than the X-ray source configuration, geometric arrangement of the detector is another important component in a cone-beam imaging system. The development in detector technology provides increasingly high resolution X-ray detectors such as the panel system. In one embodiment, a panel detector is used. Its vertical-axis is aligned to the rotational axis of the source orbit and its horizontal axis is parallel to the projection of the tangent of the source orbit at the specified source position on a horizontal plane (see FIG. 5).

Denote by S the source position. Let N be the point where the perpendicular line from the source to the detector plane meets the detector. Let the distance from the detector to the rotational axis be D, which is fixed. The center of the detector image, denoted by $O_I$, may not coincide with N particularly when the area of the detector needs to be maximumly utilized. O' denotes the intersection of the perpendicular line SN and the rotational axis. Under this detector arrangement, data acquisition geometry has a striking cylindrical symmetry. Alternatively, one can utilize the symmetry about the object center and lay the two-dimensional detector array on a plane perpendicular to the line connecting the source and the origin (as shown in FIG. 2).

In practice, the two-dimensional detector surface may be curved or may not be oriented as we described. However, we can treat the above two configurations as two standard image planes. The pixels on any detector surface can be one-to-one mapped to a chosen standard image plane 24 by a geometric transform (see FIG. 6). Given a point on a real detector, the corresponding pixel on the standard image plane is the intersection of the image plane with the line connecting the source to the point. Before getting into the details of the reconstruction steps, a geometric interpretation of the approach is provided.

Assume that a function $f$ on $R^3$ represents the three-dimensional radiation attenuation inside the object being scanned and $f$ has a finite support $\Omega$. The cone-beam image obtained from a particular point source $\Phi(\lambda)$ measures the half line integrals of attenuation along rays passing through $\Phi(\lambda)$:

$$g(\lambda, \alpha) = \int_0^{+\infty} f(\Phi(\lambda) + t\alpha) dt, \alpha \in S^2. \quad (10)$$

We name g the X-ray transform of $f$.

There are two distinguished spaces when we process the cone-beam image data. One is the object space in which the three-dimensional attenuation map of the object is to be evaluated. The other is the Radon space, or called the transform space, which is the space of all the planes in $R^3$. Object space and transform space cohabit in the same physical space but they have separate coordinate systems.

Assume that the object space is a uniformly spaced lattice in Cartesian coordinate, say $\{O: x, y, z\}$ with origin, O at the center of the object, and the z-axis is aligned with the rotational axis of the source orbit. This coordinate is called the global reference frame.

The coordinates identifying a particular Radon plane in the Radon space are $\beta$, the unit normal vector, and l, the perpendicular distance of the plane to the origin. (l, $\beta$) are the global coordinates of the Radon space. One can visualize the Radon space by attaching to each point, $x \in R^3$, a two-dimensional unit sphere, and the points on $S_x^2$ represent the unit normals of all the planes through x. This is the backprojection sphere discussed earlier. Such a representation of the Radon space is redundant since many planes passing by the object intersect with the source orbit multiple times. In the mean time, this redundant representation is advantageous in the reconstruction context since the differential-backprojection operator in the Radon formula (Eqn. (3)), when evaluated for point x, acts on $R''f$ (l, $\beta$) all or almost all planes passing through x, where l=x·$\beta$, and no other planes. The sphere $S_x^2$ is therefore handy for visualizing the geometric computation at the point x, where the function is to be recovered. In the ultimate reconstruction, however, the redundancy is taken into account and each Radon plane shall be weighted by the number of times it meets with the source orbit, which is the redundancy function.

Next, a cone-beam projection from a point source is examined. The divergent beams consist of a family of fan beam slices on those planes passing by the radiation source and an arbitrary line on the two-dimensional image plane; these planes constitute only a subset of all the planes in the projective Radon space. To be able to describe the geometric constraint raised by each cone-beam projection, a point source, say S, is selected and a projection line that connects the source S to a point P on the image plane. Then, for each point Q lying on SP, the family of planes passing by both S and Q intersect at SP. As a result, the normal directions of this set of planes are perpendicular to the projection line SP and are confined to a great circle on the backprojection sphere 26 surrounding Q (see FIG. 7). We call the great circle 28 the backprojection circle.

Figure 8:
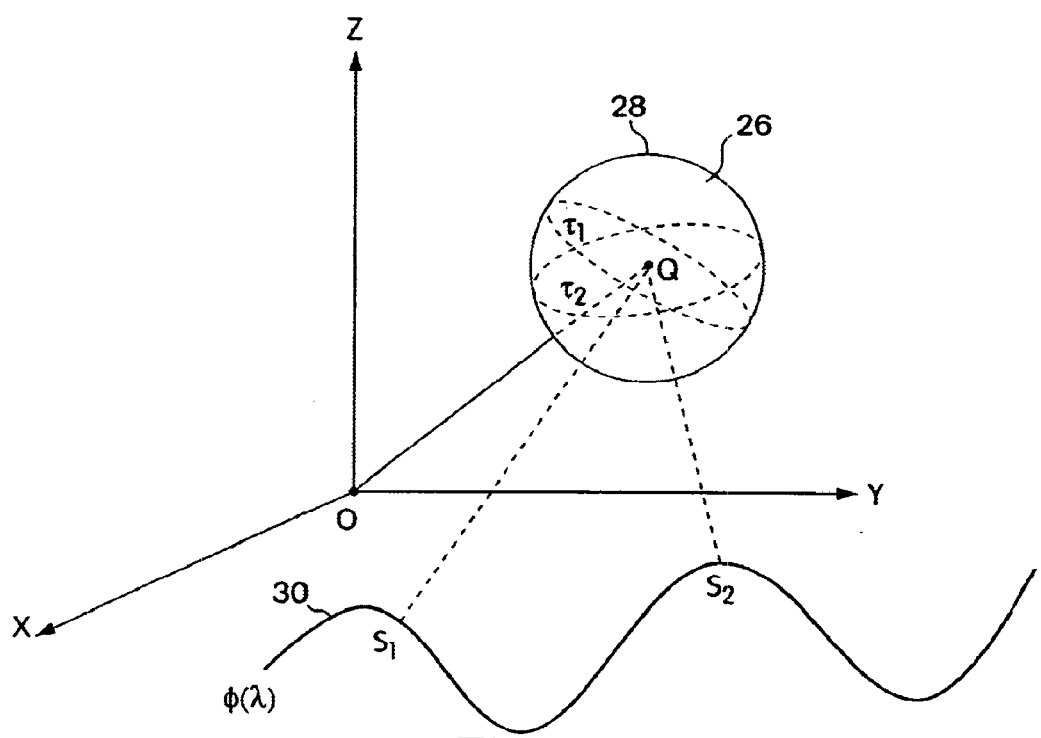
FIG. 8 illustrates the rigid rotation of the backprojection orientations from projection to projection.

As the radiation source is moved around the object, the backprojection circle seems to rotate about Q and changes its orientation while still remaining on the back-projection sphere (see FIG. 8). It is a rigid rotation. As long as the source orbit 30 satisfies the data sufficiency condition, the backprojection circles sweeps out and cover the entire backprojection sphere 26.

The geometric analysis leads to the following decomposed Radon inversion formula which is suited for three-dimensional cone-beam reconstruction:

$$f(x) = -\frac{1}{8\pi^2} \int_\Lambda \left\{ \int_{\beta \in \{x - \Phi(\lambda)\}^\perp, \beta \in S^2} R'' f(\Phi(\lambda) \cdot \beta, \beta) \frac{|\Phi'(\lambda) \cdot \beta|}{M(\lambda, \beta)} d\beta \right\} d\lambda, \quad (11)$$

where $\{x-\Phi(\lambda)\}^\perp$ denotes the plane perpendicular to $x-\Phi(\lambda)$ and through the origin. The derivative in $R''f$ acts on its first variable, and $M(\lambda, \beta)$ is the redundancy function depicting the number of times that the plane $L_{\Phi(\lambda)\beta,\beta}$ intersecting with the source orbit.

Reading from Eqn. (11), there is, at each fixed source position, only one two-dimensional backprojection that needs to be performed along each projection ray. The resulting value is constantly assigned to all the points lying on that ray.

For each cone-beam projection, it is convenient to set up a local coordinate with the origin at the source. In the first embodiment, we construct an orthonormal basis with one of the coordinate axes aligned with the rotational axis (the same as the z-axis in the global reference frame); and the other two axes synchronizing with the rotation of the source-detector pair relative to the object when viewed from a horizontal plane (see FIG. 9):

$$\begin{cases} u = \frac{1}{\sqrt{\phi_1^2(\lambda) + \phi_2^2(\lambda)}} (-\phi_2(\lambda), \phi_1(\lambda), 0) \\ v = (0, 0, 1) \\ w = \frac{1}{\sqrt{\phi_1^2(\lambda) + \phi_2^2(\lambda)}} (\phi_1(\lambda), \phi_2(\lambda), 0). \end{cases} \quad (12)$$

As $\lambda$ ranges in $\Lambda$, such a construction generates a set of 3-by-3 orthonormal matrices $O(\lambda)=(u(\lambda), v(\lambda), w(\lambda))$, which are associated with a set of consecutive rotations. The sequence of orthonormal local bases is called a moving frame basis or simply moving basis with the origin anchored on the source orbit.

The way to construct a moving basis is fairly general and flexible; there are variable choices. Preferably, the moving basis represents a natural geometric relationship within each local projection, so the resulting coordinates are simple and brings ease and efficiency into the coordinate computation. The moving basis is often characterized by a smooth evolution from one frame to the next, which allows the computation to be stream-like, more structured and trackable.

Figure 10:
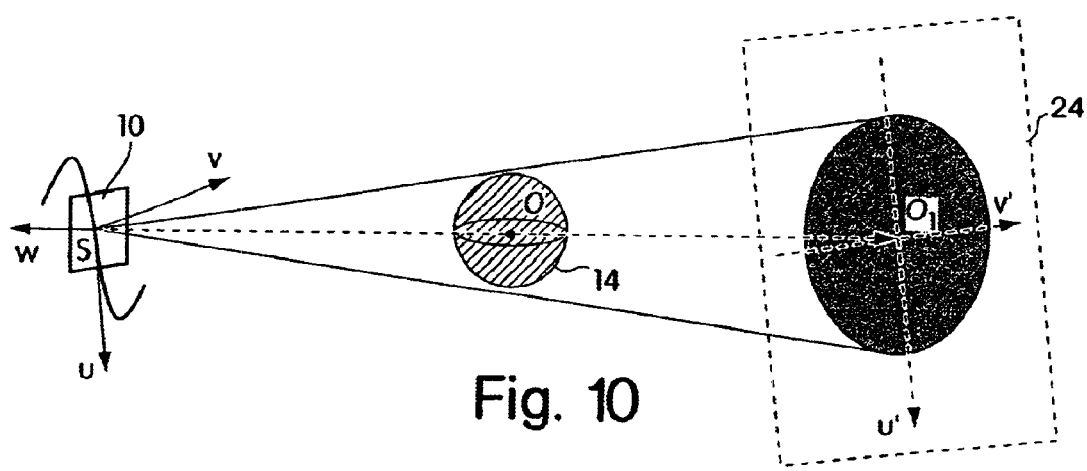
FIG. 10 provides a conceptual image of the moving basis for a second embodiment.

In the second preferred embodiment, we can construct the following orthonormal moving basis $$\begin{cases} w = \frac{\Phi(\lambda)}{|\Phi(\lambda)|} \\ v = \frac{w \times \Phi'(\lambda)}{|w \times \Phi'(\lambda)|} \\ u = v \times w \end{cases} \quad (13)$$

with origin attached to the source orbit (see FIG. 10). In both embodiments, the local axes, u and v, are aligned with the axes on the image planes, denoted by u' and v'.

Returning to Eqn. (11), the reconstruction of a three-dimensional function requires the second-order radial derivative of the Radon transform, $R''f$. This is not directly available from the X-ray transform of divergent beams. The evaluation of $R''f$ is carried out in two phases.

Figure 11:
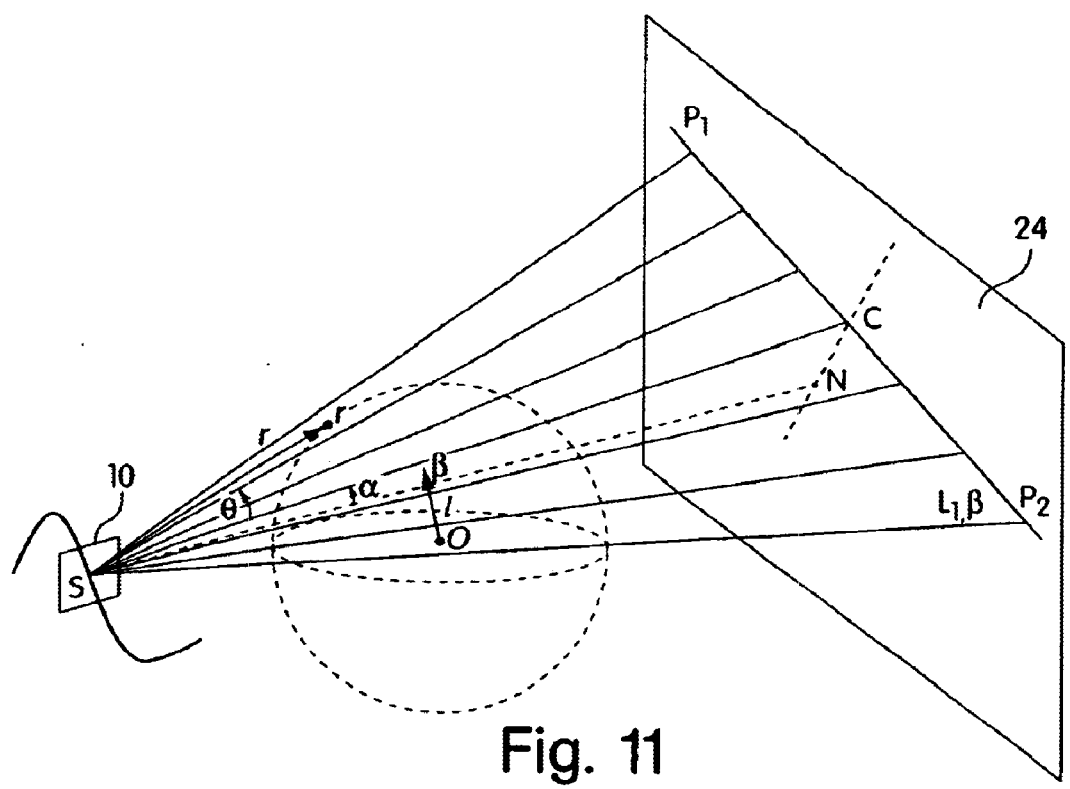
FIG. 11 provides a conceptual image of a Radon plane intersecting the image plane.

According to Grangeat's Fundamental Relation, one can obtain the first-order radial derivative of the Radon transform from cone-beam projection data. FIG. 11 illustrates a Radon plane $L_{l,\beta}$ intersecting the support of $f$. $P_1P_2$ is the intersection line between $L_{l,\beta}$ and the image plane. Let P be an arbitrary point on $P_1P_2$. Let a the angle between $L_{l,\beta}$ and the perpendicular line from the source to the image plane, SN. Note that SN may not pass through the global origin. Let the central ray be the shortest line on $L_{l,\beta}$ from the source S to the intersection line $P_1P_2$, denoted by SC. It is easy to verify that SC is perpendicular to $P_1P_2$.

Because the fan beams restricted on the plane $L_{l,\beta}$ all meet at the source, it is natural to use polar coordinates on this plane, with the origin placed at the X-ray source and the axis aligned with the central ray. Denote by r and θ the radial and angular parameters respectively in this polar coordinates. We reformulate the Fundamental Relation as follows:

$$\frac{\partial Rf(l,\beta)}{\partial l} = -\frac{\partial}{\partial \alpha}\left\{\int \frac{1}{\cos\theta}\int f(r)dr d\theta\right\} \quad (14)$$

Where the double integral is performed on the plane $L_{l,\beta}$.

Note that the inner integral in Eqn. (14), $\int f(r) dr$, for some fixed θ, represents the X-ray transform in polar coordinates on the Radon plane $L_{l,\beta}$; this is a measurement available from the cone-beam image. The double integral is the weighted line integral of the X-ray transform; the weight is the cosine of the angle between a particular ray on the Radon plane with the central ray.

Angle α serves as an intuitive link between the coordinates in the local projection frame and the coordinates in the Radon space. In each local projection frame, we are dealing only with lines (on the image plane) instead of planes. However, each line, say $P_1P_2$, on the image plane is associated to a plane that passes through the source point and intersects the plane by $P_1P_2$.

Figure 12:
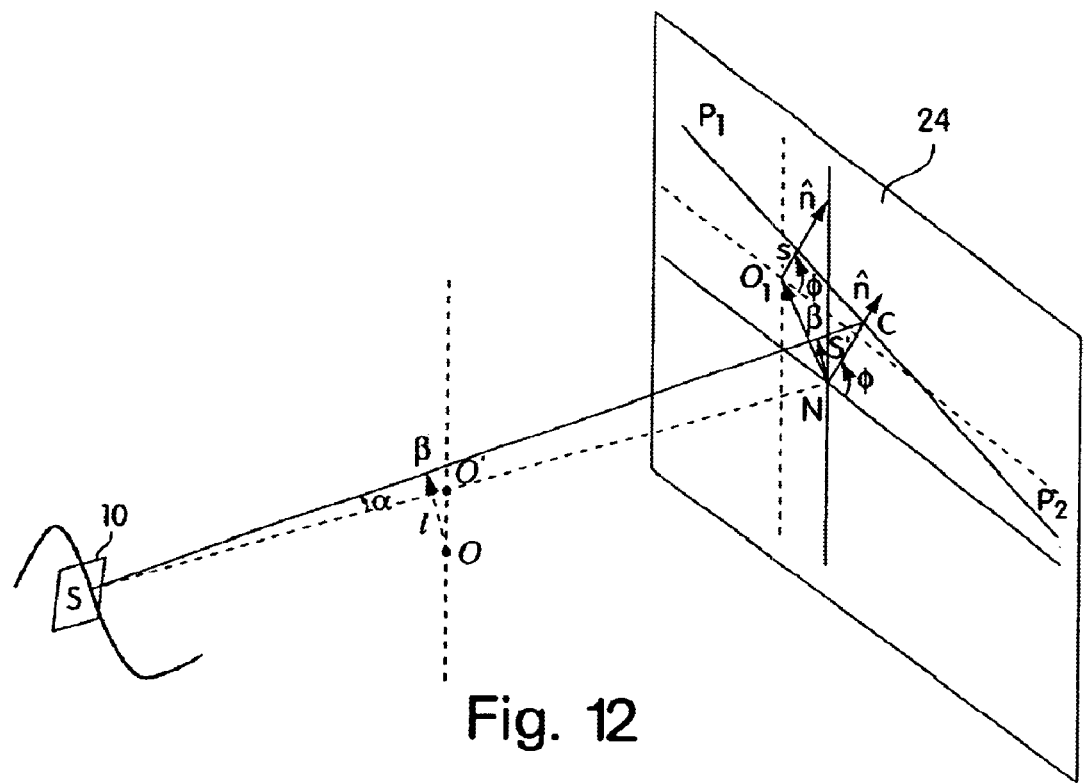
FIG. 12 illustrates how the cone-beam slice angle links the global coordinates in the Radon space and the local coordinates on the image plane.

On the image plane, assume that the radial distance of the intersection line $P_1P_2$ from the image center is s and its normal direction, n, form an angle φ with the u'-axis (see FIG. 12).

If the center of the image $O_I$ is aligned to the perpendicular line from the source to the image plane, SN, then (s,φ) can be expressed as $$\begin{cases} \phi = \arctan\left(\frac{\beta \cdot u}{\beta \cdot v}\right) \\ s = (R+D)\tan\alpha \end{cases} \quad (15)$$

If N is off center on the image plane, the radial distance should be offset by the projection of $NO_I$, onto the unit normal, e.g., n=(cos φ, sin φ), of $P_1P_2$, whereas the angle φ is preserved. It yields $$\begin{cases} \phi = \arctan\left(\frac{\beta \cdot u}{\beta \cdot v}\right) \\ s = (R+D)\tan\alpha - NO_I \cdot n \end{cases} \quad (16)$$

Eqn. (15)–(16) link the α-coordinate to the s-coordinate. Hence, s is a function of α. The partial derivative with respect to α in Eqn. (14) can then be evaluated through the radial derivative of the weighted line integrals on the image plane by $$\frac{\partial}{\partial \alpha} = \frac{R+D}{(1-\tan^2\alpha)}\frac{\partial}{\partial s}. \quad (17)$$

The image plane has only discrete samples; in other words, there is no real image lines on a image plane. Then the question is, what is the suitable representation of lines on a discrete grid? A line that is represented by the discrete samples on the image plane is called a virtual image line. Under symmetry consideration, we can generate a set of parallel lines with rational slopes in such a way that there are exactly the same number of lines passing through every image pixel (see FIG. 13). Note that a rational slope means it is a ratio of two integers, which allows the set of virtual lines to pass through as many grid nodes as possible.

The fact that the slopes are rational helps to align the pixels on the image plane, which offers great efficiency since the weighted line integral is calculated only once for all the pixels lying on the same rational line. Besides, data interpolation can be done in a very systematic and symmetric way; data points falling between two adjacent nodes can be linearly interpolated from the grid values with weights determined by the separation distance from each neighboring node (see FIG. 14).

For each rational line, say $P_1P_2$, on the image plane, there is a corresponding plane passing by the source and intersects the image plane by $P_1P_2$. The global coordinates of the plane in the Radon space, (l, β), can be estimated by $$\begin{cases} \beta = \frac{SP_1 \times SP_2}{|SP_1 \times SP_2|} \\ l = \Phi(\lambda) \cdot \beta \end{cases} \quad (18)$$

Hence, from the line calculation on the image plane we obtain the first-order radial derivative of the Radon transform on a set of two-dimensional planes. The set of selected rational lines determines a set of planes whose coordinates are given by Eqn. (18).

To evaluate the second-order radial derivative of the Radon transform, we construct a set of planes parallel to the planes selected in estimating the first-order Radon derivatives. Since the planes passing by a single source point are non-parallel, the second-order radial derivative of the Radon transform is not available from one cone-beam projection. This second differentiation shall be carried out over the parallel planes from nearby projection frames (See FIG. 15).

The partial derivative with respect to the radial distance, l, is related to the partial derivative with respect to the source orbit parameter, λ, by $$\frac{\partial}{\partial l} = \frac{1}{\Phi'(\lambda) \cdot \beta}\frac{\partial}{\partial \lambda}. \quad (19)$$

In order to find the set of planes in the next cone-beam projection frame parallel to the set of planes chosen by the current projection, we can utilize the method of moving frames. Assume $(l_1, \beta)$ is the global coordinate of a Radon plane processed by the current projection, with $l_1=\Phi(\lambda_1)*\beta$.

Figure 16:
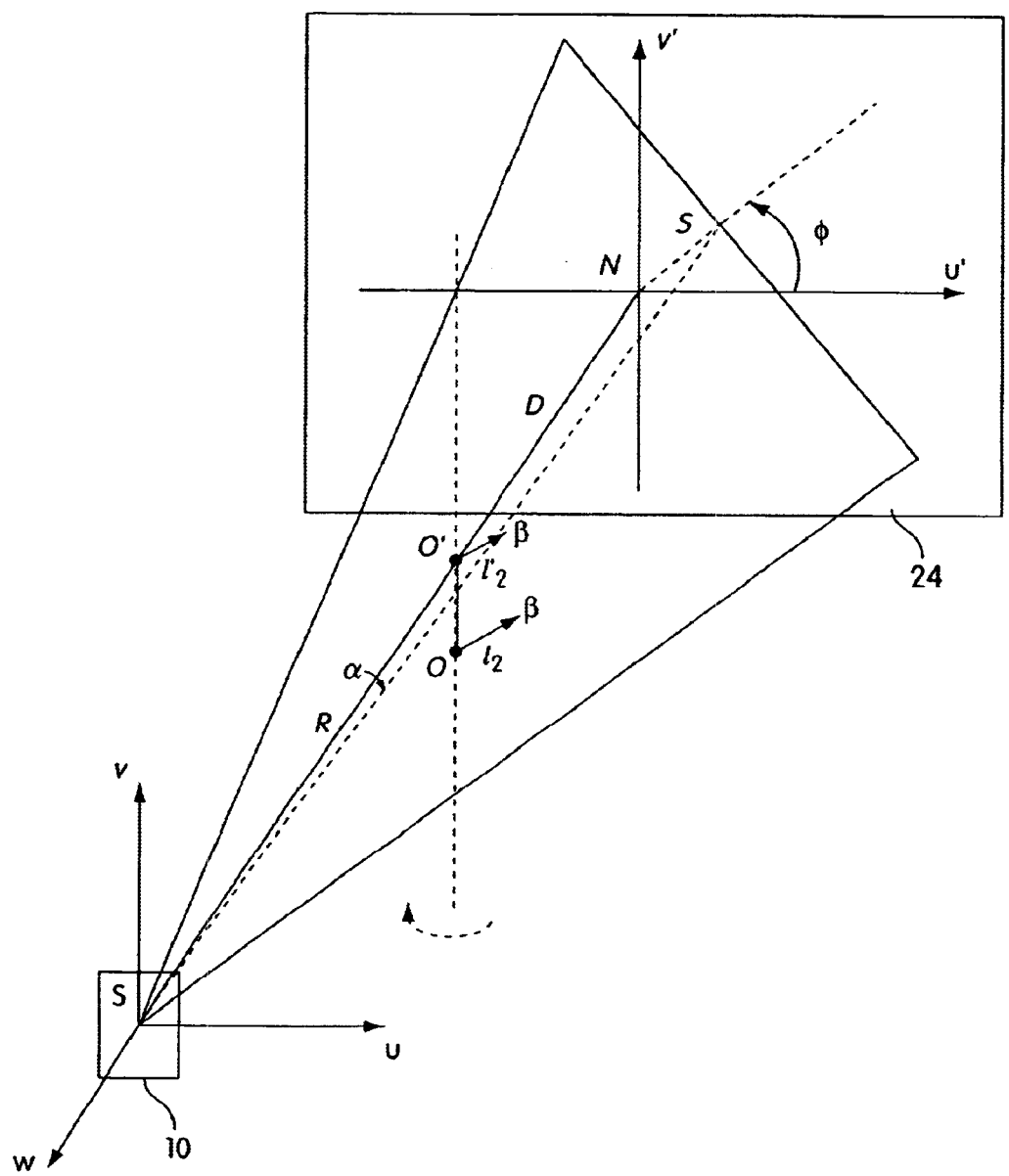
FIG. 16 offers a visualization of how a local basis of a line on the image plane is determined by the global coordinates of a Radon plane as well as a moving basis.

In the subsequent projection, the global coordinates of the plane passing by the next source point $\Phi(\lambda_2)$ and parallel to $L_{l1,\beta}$ is given by $(l_2,\beta)$, with the same unit normal and with $l_2=\Phi(\lambda_2)*\beta$. Again, we are dealing with lines instead of planes in the local projection frame. If the perpendicular line from the source to the detector passes through the global origin, as in the second embodiment, the radial distance and the angular variable, (s,φ), of the intersection line between the plane $L_{l2,\beta}$ and the image plane is given by $$\begin{cases} s = (R+D) \cdot \dfrac{l_2}{\sqrt{R^2 - l_2^2}} \\ \phi = \arctan\left(\dfrac{\beta \cdot u}{\beta \cdot v}\right) \end{cases} \quad (20)$$

in which s is obtained by eliminating $\alpha$ from $\sin \alpha = l_2/R$ and $\tan \alpha = s/(R+D)$ (see FIG. 16).

In the first embodiment, the perpendicular line from the source to the image plane does not pass through the global center; as a result, the radial distance of the plane $L_{\Phi(\lambda 2) \cdot \beta, \beta}$ is offset by $OO' \cdot \beta$. Replacing $l_2$ by $l_2 + O\tilde{O} \cdot \beta$ in Eqn. (20), we obtain the local coordinates of the intersection line from the second cone-beam image associated to the parallel plane.

The second-order Radon derivative can therefore be evaluated by subtracting the first radial derivative of the Radon transform obtained from two consecutive cone-beam images and dividing by $\Phi(\lambda_2) \cdot \beta - \Phi(\lambda_1) \cdot \beta$. This is essentially the first order approximation through a one-step finite difference. Higher order approximation can be achieved by engaging more cone-beam images. It means that a few more images shall be acquired in advance.

The result is weighted by the multiplicity of each plane intersecting with the source orbit. For the quadratic curve family we have given explicit instructions for finding such intersections, as noted above.

Figure 17:
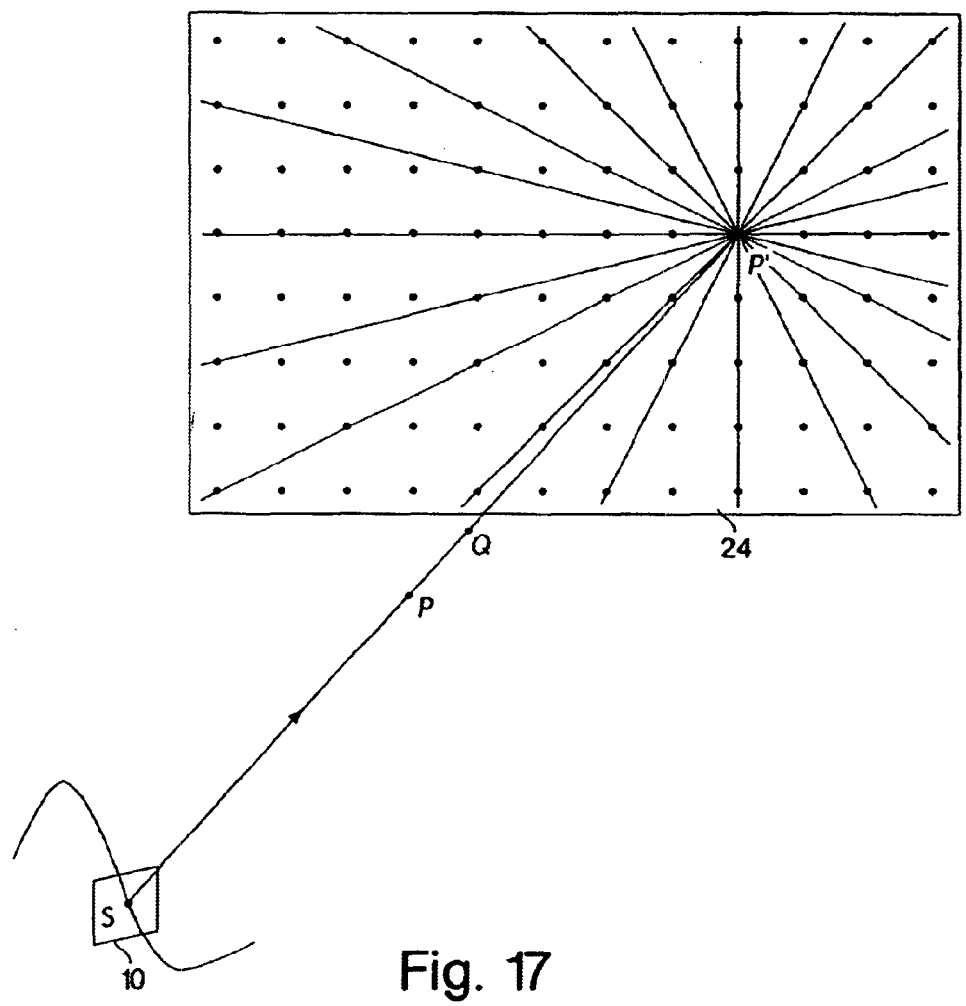
FIG. 17 provides a visualization of sampled planes passing by the same projection line meeting the image plane at a set of rational lines.

So now, for each node on the image plane, we obtained the second-order radial derivative of the Radon transform on a set of planes corresponding to a set of rational lines passing through the same pixel (see FIG. 17).

This discrete data set is then used to approximate the two-dimensional backprojection on the unit circle perpendicular to the projection line from the source to the image node by $$\sum_{j=0}^{N-1} R'' f(\Phi(\lambda) \cdot \beta_j, \beta_j) \frac{|\Phi'(\lambda) \cdot \beta_j|}{M(\Phi(\lambda) \cdot \beta_j, \beta_j)} \Delta \theta_j \quad (21)$$

where $\beta_j$'s are unit normals of the processed planes and $\theta_j$'s are the angular intervals between $\beta_j$'s.

For a given node on the image plane, the projection line connects this node to the source and is constantly valued by the result of the two-dimensional backprojection. The rays emitting from a single source point are projective whereas the object space is represented by a Cartesian grid. As a result, the local and the global coordinates are characterized by different sampling patterns (see FIG. 18). The projection rays are resampled and interpolated to obtain the nodal values on the Cartesian grid. The simplest interpolation scheme is the nearest neighbor method, i.e., finding the closest line for each Cartesian node and assigning the value of its closest neighbor to it. Higher-order approximation can be achieved by involving more neighboring projection lines.

It is clear that the two-dimensional backprojections yield a three-dimensional image. We call the resulting three-dimensional image a local reconstruction because it is reconstructed from a single projection and its adjacent cone-beam projections, which provide only partial information about the object. Each local reconstruction does not discriminate the variations along each projection line.

The above process is repeated until the cone-beam data acquisition is complete. The ultimate three-dimensional reconstruction is the sum of all the intermediate, locally reconstructed images which can be carried out accumulatively and simultaneously with the scanning and reconstruction process. The contributions from all the local reconstructions are equally weighted. The final output is a three-dimensional array that can be displayed on a computer screen using proper computer graphics engine, either in the slice-by-slice two-dimensional format or in the form of a computer-rendered three-dimensional anatomical representation. It can also be kept in a storage-media for future use.

The moving frame reconstruction paradigm outlined herein can be applied to general cone-beam imaging systems with variable scan paths and detector configurations. When applied, minor details may differ, i.e., the choice of a specific moving basis, or using different sampling and interpolation schemes, etc.; the principle that allows accurate and systematic calculation of the second-order radial derivative of the Radon transform via the method of moving frames does not depart.

While this invention has been shown and described with references to particular embodiments thereof, those skilled in the art will understand that various changes in form and details may be made therein without departing from the scope of the invention, which is limited only by the following claims.

What is claimed is:

1. A method for generating a three-dimensional image of a scanned object from a plurality of cone-beam projections passed through the object and attenuated thereby, the method comprising:
   a) positioning the source at an initial position on a predetermined scan path;
   b) passing a projection of cone-beam radiation comprising a plurality of projection rays from a common focal point through an object, the cone-beam projection being attenuated by partial absorption in the object;
   c) detecting radiation intensity of the attenuated cone-beam projection on an area detector;
   d) obtaining a two-dimensional attenuation image of the cone-beam projection from the detected radiation intensity;
   e) obtaining an intermediate transform function from the two-dimensional attenuation image on a set of planes passing through the focal point;
   f) at least once, repositioning the source and repeating steps (b)–(e);
   g) filtering the intermediate transform functions acquired from consecutive attenuation images at two or more source positions using a moving-frame technique to obtain the second-order radial derivative of the Radon transform;
   h) backprojecting the second-order radial derivative of the Radon transform in a two-dimensional space along each projection ray to generate an intermediate, locally reconstructed, three-dimensional image with constant values assigned along each projection ray;
   i) at least once, repeating steps (f)–(h); and
   j) summing the plurality of intermediate, locally reconstructed, three-dimensional images obtained for the plurality of cone-beam projections to obtain an ultimate, reconstructed, three-dimensional image of the object.

2. The method of claim 1, wherein the intermediate transform function is the first-order radial derivative of the Radon transform.

3. The method of claim 2, wherein each two-dimensional attenuation image is obtained as a discrete two-dimensional data set with an area detector comprising a plurality of detector elements, and wherein the step of obtaining the first-order radial derivative of the Radon transform includes:

i) if the area detector does not coincide with the standard image plane:
   a) mapping the coordinates of the detector elements to the coordinates of a set of points on a standard image plane under a projective coordinate transform; and
   b) interpolating the two-dimensional data set to obtain attenuation values on a regular grid on the standard image plane;
ii) interpolating data points lying between grid nodes along a set of virtual image lines;
iii) calculating a weighted sum of attenuation along each virtual image line with weights determined by the cosine of the angle between (a) a projection ray associated to a image point and (b) a central ray, which is the shortest line from the source to the virtual image line;
iv) differentiating the weighted sum over a set of parallel image lines to obtain the first-order radial derivative of the Radon transform on a set of corresponding planes passing through the focal point; and
v) storing the resulting first-order radial derivative of the Radon transform in memory for use in a subsequent phase of reconstruction.

4. The method of claim 3, wherein the virtual image lines are rational lines.

5. The method of claim 3, wherein the regular grid has square or rectangular elements.

6. The method of claim 1, wherein the two-dimensional backprojection along a projection ray is an integral over all planes passing by that ray, wherein the unit normal vectors of these planes are confined to a great circle on the unit sphere.

7. The method of claim 1, wherein a plurality of cone-beam projections are successively passed through the object, and wherein the step of determining the second-order radial derivative of the Radon transform includes:

i) obtaining the first-order radial derivative of the Radon transform on a set of planes for the next one or more cone-beam projections;
ii) determining the global coordinates, represented by the unit normal and radial distance, of a set of corresponding planes that pass though a set of virtual image lines on the standard image plane and through the focal point;
iii) calculating the local parameters of intersection image lines between the image plane and corresponding planes in successive cone-beam projections parallel to the set of planes passing through the focal point via a coordinate transformation determined by a moving-frame basis;
iv) interpolating the first-order radial derivative of the Radon transform for the planes obtained in part (iii) from the first-order radial derivative of the Radon transform obtained in part (i); and
v) obtaining the second-order radial derivative of the Radon transform by differentiating, which can be approximated by a finite difference, the first-order radial derivative of the Radon transform over the parallel planes from consecutive cone-beam projections.

8. The method of claim 1, wherein the step of backprojecting the second-order radial derivative includes:

for each projection ray associated with a node on the image plane, calculating a weighted sum of the second-order radial derivative of the Radon transform over a set of planes passing through the projection ray with weights determined by the number of intersections of each plane with the scan path and by the angular interval between two adjacent planes, wherein the weighted sum is constantly-assigned to all points along the projection ray; and resampling and interpolating the projection rays so that each node on a three-dimensional Cartesian grid representing the object is positioned on one of the rays and is assigned a value to produce a three-dimensional, locally reconstructed image.

9. The method of claim 1, wherein the source is displaced along a complete scan path relative to the object, wherein the scan path intersects with almost all planes passing by the object and the scan path is everywhere differentiable, with exception allowed for a zero measure set, and the cone-beam is generated and passed through the object at a plurality of locations on the complete scan path.

10. The method of claim 9, wherein the scan path is a biquadratic curve.

11. The method of claim 1, wherein the radiation is X-ray radiation.

12. The method of claim 1, wherein the cone-beam projections are detected with an area detector on an opposite side of the object from the radiation source.

13. The method of claim 1, wherein the area detector has a vertical axis parallel with the rotational axis and a horizontal axis parallel with the projection of the tangent line of the scan path at a current source position onto a horizontal plane.

14. The method of claim 1, wherein the detector is placed orthogonal to a line connecting the source to the center of the object, and the horizontal axis of the detector is aligned with the projection of the tangent of the scan path at a current source position onto a surface of the detector.

15. The method of claim 1, wherein the moving frame technique involves the generation of a set of orthonormal bases with the origin of each orthonormal basis positioned at a focal point such that each time the source is repositioned to generate a new focal point and the two-dimensional attenuation image is obtained, the orthonormal basis has a new origin, wherein the moving frame technique enables the second-order radial derivative of the Radon transforms to be evaluated by filtering over a set of parallel planes from consecutive cone-beam projections.

16. The method of claim 15, wherein the moving frame technique enables location of the parallel planes from a set of coordinate transforms.

17. A computer system for generating a reconstruction of cone-beam radiation attenuation in an object, the computer system comprising:

means for obtaining an intermediate transform function from a signal representing the amount of radiation transmitted through the object;

means for calculating the second-order radial derivative of the Radon transform by filtering the intermediate transform function over a pair of or multiple consecutive two-dimensional cone-beam measurement using a moving-frame technique;

means for backprojecting the second-order radial derivative of the Radon transform to generate an intermediate, locally reconstructed, three-dimensional image with constant values assigned along each projection ray; and an accumulation buffer to sum the plurality of intermediate, locally reconstructed, three-dimensional images obtained for the cone-beam projections to obtain an ultimate, reconstructed, three-dimensional image of the object.

18. A computer-readable storage medium storing computer-executable software for generating a reconstruction of cone-beam radiation attenuation in an object, the software comprising:

code for obtaining an intermediate transform function from a signal representing the amount of radiation transmitted through the object;

code for calculating the second-order radial derivative of a Radon transform by filtering over the intermediate transform function using a moving-frame technique;

code for backprojecting the second-order radial derivative of the Radon transform to generate an intermediate, partially reconstructed, three-dimensional image with constant values assigned along each projection ray; and code for summing the plurality of intermediate, locally reconstructed, three-dimensional images obtained for the cone-beam projections to obtain an ultimate, reconstructed, three-dimensional image of the object.

19. A cone-beam tomography apparatus comprising a computer-readable storage medium storing computer-executable software for generating a reconstruction of cone-beam radiation attenuation in an object, the software comprising:

code for obtaining an intermediate transform function from a signal representing the amount of radiation transmitted through the object;

code for determining the second-order radial derivative of the Radon transform by filtering over the intermediate transform function using a moving-frame technique;

code for backprojecting the second-order radial derivative of the Radon transform to generate an intermediate, locally reconstructed, three-dimensional image with constant values assigned along each projection ray; and code for summing the plurality of intermediate, locally reconstructed, three-dimensional images obtained for the cone-beam projections to obtain an ultimate, reconstructed, three-dimensional image of the object.

20. The cone-beam tomography apparatus of claim 19, further comprising a radiation source, a radiation detector and a support for an object to be scanned by radiation from the radiation source.

21. The cone-beam tomography apparatus of claim 20, wherein the software further comprises code for displacing the source and detector relative to the support to provide a biquadratic scan path for radiation transmitted from the source, through an object positioned by the support, and to the detector.

22. A cone-beam tomography apparatus for generating a reconstruction of cone-beam radiation attenuation in an object, the apparatus comprising means for obtaining an intermediate transform function from a signal representing the amount of radiation transmitted through the object;

means for determining the second-order radial derivative of the Radon transform by filtering over the intermediate transform function using a moving-frame technique;

means for backprojecting the second-order radial derivative of the Radon transform to generate an intermediate, locally reconstructed, three-dimensional image with constant values assigned along each projection ray; and means for summing the plurality of intermediate, locally reconstructed, three-dimensional images obtained for the cone-beam projections to obtain an ultimate, reconstructed, three-dimensional image of the object.

* * * * *

UNITED STATES PATENT AND TRADEMARK OFFICE
CERTIFICATE OF CORRECTION

PATENT NO. : 6,944,259 B2
APPLICATION NO. : 10/256727
DATED : September 13, 2005
INVENTOR(S) : Yang It is certified that error appears in the above-identified patent and that said Letters Patent is hereby corrected as shown below:

The title page, showing an illustrative figure, should be deleted and substitute therefor the attached title page.

Delete Column 1 line 1 through Column 18 line 36 and insert Column 1 line 1 through Column 18 line 51 as attached.

Signed and Sealed this

Ninth Day of November, 2010

David J. Kappos
*Director of the United States Patent and Trademark Office*

United States Patent
Yang

(10) Patent No.: US 6,944,259 B2
(45) Date of Patent: Sep. 13, 2005

(54) VERSATILE CONE-BEAM IMAGING APPARATUS AND METHOD

(75) Inventor: Xiaochun Yang, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 180 days.

(21) Appl. No.: 10/256,727

(22) Filed: Sep. 26, 2002

(65) Prior Publication Data

US 2003/0072406 A1 Apr. 17, 2003

Related U.S. Application Data

(60) Provisional application No. 60/325,055, filed on Sep. 26, 2001.

(51) Int. Cl.[7] ................................................ A61B 6/03
(52) U.S. Cl. ................... 378/15; 378/4; 378/8; 378/901
(58) Field of Search ............................ 378/15, 8, 4, 901

(56) References Cited

U.S. PATENT DOCUMENTS

| 5,592,523 | A  | 1/1997  | Tuy et al.      |
| 5,625,660 | A  | 4/1997  | Tuy             |
| 5,805,659 | A  | 9/1998  | Tam             |
| 5,926,521 | A  | 7/1999  | Tam             |
| 5,933,517 | A  | 8/1999  | Grangeat et al. |
| 5,999,587 | A  | 12/1999 | Ning et al.     |
| 6,219,441 | B1 | 4/2001  | Hu              |
| 6,275,561 | B1 | 8/2001  | Danielsson      |
| 6,285,733 | B1 | 9/2001  | Proksa et al.   |
| 6,292,525 | B1 | 9/2001  | Tam             |
| 6,411,670 | B1 | 6/2002  | Besson          |
| 6,574,299 | B1 | 6/2003  | Katsevich ........... 378/14 |
| 6,627,893 | B1 * | 9/2003 | Zeng et al. ........ 250/363.04 |

FOREIGN PATENT DOCUMENTS

| EP | 0292402      | 11/1988 |
| WO | WO 99/01066  | 1/1999  |
| WO | WO 01/06931  | 2/2001  |
| WO | WO 01/60236  | 8/2001  |

OTHER PUBLICATIONS

International Search Report for PCT US 02/30794, mailed Feb. 13, 2003.*
Tang and Ning (2001) "A cone beam filtered backprojection (CB-FBP) reconstruction algorithm for a circle-plus-two-arc orbit" Med. Phys. 28(6):1042–1055.*

* cited by examiner

Primary Examiner—David V. Bruce
Assistant Examiner—Elizabeth Gemmell
(74) Attorney, Agent, or Firm—Robert J. Sayre; Mintz, Levin, Cohn, Ferris, Glovsky and Popeo, P.C.

(57) ABSTRACT

A three-dimensional image of an object scanned with a plurality of cone-beam projections from a number of source positions is reconstructed using a method wherein intermediate transform functions are obtained from two-dimensional images of radiation attenuation in the scanned object. The intermediate transform functions are then filtered over a set of parallel planes using a moving-frame technique. The second-order radial derivative of the Radon transform can then be backprojected to generate an intermediate, locally-reconstructed, three-dimensional image. After repetition of this process, the plurality of intermediate, locally reconstructed, three-dimensional images are summed to obtain an ultimate, reconstructed, three-dimensional image of the object.

22 Claims, 11 Drawing Sheets

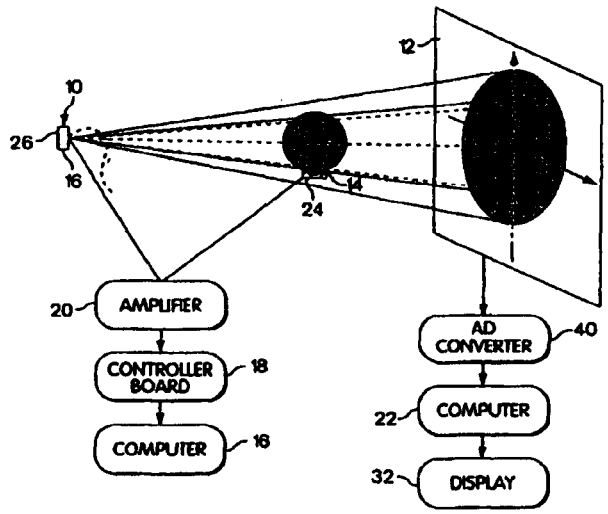

VERSATILE CONE-BEAM IMAGING APPARATUS AND METHOD

RELATED APPLICATION

This application claims priority to provisional patent application, U.S. Ser. No. 60/325,055, filed 26 Sep. 2001, the entire teachings of which are incorporated herein by reference.

BACKGROUND

Cone-beam computerized tomography (CT) reconstructs the absorption function of a three-dimensional object from a set of cone-beam projections. Such a system uses an area detector to receive rays emitted from an X-ray point source and attenuated by partial absorption in the object that they pass through. As in traditional (i.e., planar) CT, the source 10 and the detector 14 are placed on opposite sides of the object 12 being scanned (see FIG. 1). Rays contributing to an image on the detector surface form a cone with the X-ray source 10 at the apex. From the X-ray radiance value recorded at a point on the area detector 14, one can compute the integral of attenuation along the ray from the X-ray source 10 to the given point on the detector 14.

As the source-detector 10/14 pair undergoes a simultaneous rotation and translation around the object 12, a plurality of two-dimensional cone-beam images projected from various source positions can be acquired and used to reconstruct the distribution of absorption inside the three-dimensional object 12.

Compared to the traditional slice-at-a-time tomographic machine, the cone-beam CT offers faster scans, higher patient throughput, significant reduction in X-ray dosage, and isotropic resolution. It has a great potential to be applied to a wide range of medical and industrial applications.

Radon's 1917 inversion formula (Johann Radon "Über die Bestimmung von Funktionen durch ihre Integralwerte l ängs gewisser Mannigfaltigkeiten," *Ber. Verh. Sächs. Akad. Wiss. Leipzig. Math. Nat. Kl.*, Vol. 69, pp. 262-277, 1917) plays an important role in understanding the cone-beam reconstruction problem. The building blocks of the three-dimensional Radon inversion formula are planar integrals. We can write a plane in $R^3$ as $$L_{l,\beta} = \{x \in R^3 | x \cdot \beta = l, l \geq 0, \beta \in S^2\}, \quad (1)$$

where $\beta$ is the unit normal of the plane and l is the perpendicular distance of the plane from the origin. The Radon transform of a function f on $R^3$ is defined as the set of integrals of f over all the planes in $R^3$ which can be expressed as a function of two parameters (l and $\beta$):

$$Rf(l, \beta)T := \int_{x \in L_{l,\beta}} f(x) dx. \quad (2)$$

The Radon formula is given by:

$$\left(f(x) = -\frac{1}{8\pi^2} \int_{S^2} \frac{\partial^2 Rf(l,\beta)}{\partial l^2}\bigg|_{l=x\cdot\beta} d\beta, x \in \Omega. \right. \quad (3)$$

in which, $S^2$ denotes the two-dimensional unit sphere in $R^3$ and $\Omega$ denotes the support of f. The integral in Eqn. (3) over $S^2$ is the backprojection operator; it integrates over all the planes passing through x. The integration sphere is therefore called the backprojection sphere with its center at x, denoted by $S_x^2$ (x is considered as an index). It is clear that the po on $S_x^2$ represent the unit normals of all the planes throug To recover the function value at point x, $R''f(l,\beta)$ obtained on all or almost all planes passing through x cone-beam reconstruction, however, planar integrals are available from the cone-beam data because rays dive from the point source inside each projection. Hence, Radon formula (Eqn. (3)) is not immediately employed.

The first cone-beam inversion formula for real-val functions is given by Tuy in 1983; this formula wa Fourier-based method (Heang K. Tuy "An Inversion I mula for Cone-Beam Reconstruction," *SIAM J. Appl. M* Vol. 43, 1983, pp. 546-552). Smith's paper in 1985 est lished connections between the cone-beam data and second-order radial derivative of the Radon transform, l (Bruce D. Smith "Image Reconstruction from Cone-Be Projections: Necessary and Sufficient Conditions ; Reconstruction Methods," *IEEE Trans. Med. Imag.*, Vol 1985, pp. 14-25). The most important contribution in th early derivations is a clear understanding of the data su ciency condition for an exact reconstruction, that is, aln all planes passing by the support of the object shall inter: with the source orbit.

The next significant breakthrough came with the disc ery of the Fundamental Relation by Grangeat (Pie Grangeat "Mathematical Framework of Cone-Beam Reconstruction via the First Derivative of the Rac Transform," *Mathematical methods in tomography, Lect notes in mathematics* 1497, 1991, pp.66-97. The Fundam tal Relation relates the cone-beam data on a slice of f beams inside each cone-beam projection to the first-or radial derivative of the Radon transform, $R'f$. $R'f$ serves an implicit link between the cone-beam data and $R''f$. 1 second-order radial derivative of the Radon transform needed in order to use Eqn. (3); $R''f$ is then backprojectec recover f.

Though substantial progress has been made during the l two decades, the solutions for exact cone-beam reconstr tion are still not fully satisfying. In many of the reconstr tion methods that have been developed, the backprojecti differentiation operation inherited from the Radon form appears ad hoc and is the most time-consuming step in reconstruction.

The well-known filtered backprojection (FBP) cone-be reconstruction technique, which is widely used in indust is given by Feldkamp (FDK) et al. for circular source ort (L. A. Feldkamp, L. C. David and J. W. Kress "Practi Cone-Beam Algorithm," *J. Opt. Soc. Am. A.*, Vol. 1, No. 1984, pp. 612-619). In such a case, data from cone-bea with narrow angles is treated in an approximate way usi extensions of two-dimensional fan-beam methods. The FI algorithm is easy to implement; however, it only provic reasonably good reconstruction near the mid-plane and ca not be used for wide cone angles. Hence, alternative recc struction methods and the embodying imaging apparatus ; still being sought, particularly for the large-detector cor beam system since it has become a reality.

In designing a dedicated cone-beam imaging syste finding a proper source orbit is a challenge. The selection a good source orbit not only depends on the dimension of t object under investigation, but also depends on the geom ric measurements such as the allowed source-to-object a detector-to-object separation. An important condition accurate reconstruction is the data sufficiency conditic Another desirable feature of the selected source orbit is sy: metry.

Among various source orbits that have been propos sinusoidal trajectory and helical trajectory meet both con tions. Though advantageous in their sampling performance, reconstruction procedure using these two scan paths have yet to achieve the desired efficiency. The principal difficulty encountered in the reconstruction is caused by the sophisticated mapping from the local projection geometry to the Radon space geometry characteristic to many non-planar source orbits.

Other approaches use two orthogonal planar trajectories such as circle-plus-circle, circle-plus-line and circle-plus-arc to fulfill the data sufficiency condition. Although the hybrid methods combine cone-beam data from two simpler scanning processes, they have two major disadvantages. First, the discontinuity in the mechanical movement makes them less attractive in practice. Second, sampling in the Radon space where the backprojection takes place is not balanced under these hybrid scanning geometries; this limits the reconstruction accuracy.

SUMMARY

A novel algorithmic paradigm for three-dimensional image reconstruction from cone-beam projections is disclosed, wherein a new class of algorithms, referred to as moving frame reconstruction (MFR) algorithms, is introduced. MFR algorithms have the ability to invert a set of cone-beam images progressively and simultaneously in conjunction with the X-ray scanning process.

In terms of the reconstruction procedure, the most complex and expensive computation in cone-beam imaging lies in the backprojection-differentiation operation. Described herein is a technique that enables systematic implementation of the backprojection-differentiation operation and which can be described by the following procedures.

A radiation source is initially positioned on a predetermined scan path. The source generates projection of cone-beam radiation from a common focal point. The projection, which comprises a plurality of projection "rays," passes from the source through the object, and the object attenuates the cone-beam projection as it passes therethrough. The radiation intensity of the attenuated cone-beam image is then detected on an area detector, and a two-dimensional attenuation image of the cone-beam projection is obtained from the detected radiation intensities.

From each two-dimensional attenuation image, an intermediate transform function is obtained on a set of planes passing through the focal point. The source is then repositioned and these steps are repeated.

After two or more repetitions of the above steps, the intermediate transform functions acquired from consecutive attenuation images are filtered using a moving-frame technique to obtain the second-order radial derivative of the Radon transform. The second-order radial derivative of the Radon transform is then backprojected in two-dimensional space along each projection ray to generate an intermediate, locally reconstructed, three-dimensional image with constant values assigned along each projection ray. The procedure comprising repositioning the source; obtaining (a) a two-dimensional attenuation image, (b) an intermediate transform function, and (c) a second-order radial derivative of the Radon transform; and then backprojecting that second-order radial derivative of the Radon transform is then repeated at least once.

Finally, the plurality of intermediate, locally reconstructed, three-dimensional images are summed to obtain an ultimate, reconstructed, three-dimensional image of the object.

In one embodiment, the method for performing the above-described steps of backprojecting the second-order radial derivative and summing the plurality of intermediate, locally reconstructed, three-dimensional images can be expressed as the following decomposed Radon formula:

$$f(x) = -\frac{1}{8\pi^2} \int_\Lambda \left\{ \int_{\beta \in \{l-\Phi(\lambda)\}^\perp, \beta \in S^2} R'' f(\Phi(\lambda) \cdot \beta, \beta) \frac{|\Phi'(\lambda) \cdot \beta|}{M(\lambda, \beta)} d\beta \right\} d\lambda. \quad (4)$$

where $\Phi(\lambda)$ is a complete path and is analytic, which means infinitely differentiable. $M(\lambda, \beta)$ is the number of times that a plane passing by $\Phi(\lambda)$ and having unit normal $\beta$ intersects with the source orbit. The described plane can be written as $L_{l,\beta}$, where $l = \Phi(\lambda) \cdot \beta$. Hence the function $M(\lambda,\beta)$ is also considered as a function of $l$ and $\beta$; without confusion, we can write it as $M(l, \beta)$, and it is referred to as the redundancy function.

The above mathematical formulism serves two prevailing geometric constraints underlying most of the cone-beam tomographic systems.

First, within each cone-beam projection, all the planes passing through a particular projection line have normals perpendicular to the same projection ray. As a result, backprojection orientation can be constrained onto a unit circle. This reduction of the backprojection from three-dimensional space to two-dimensional space brings great efficiency to the reconstruction method.

Second, as a radiation source traverses along the source orbit, each backprojection orientation undergoes a rigid rotation that can be described by a moving basis (e.g., determined by the local properties of the source orbit). The moving basis serves as a coordinate transform from the local projection frame to the global coordinates in the Radon space. As long as the source orbit satisfies the data sufficiency condition, one can succeed in decomposing the three-dimensional backprojection into a series of two-dimensional backprojections in accordance with the scanning geometry.

The source trajectory can be stored as software code in a computer-readable medium coupled with a computer processor. The processor, in turn is coupled with mechanical apparatus for moving the source along the source trajectory, and the processor following the instructions of the code so directs the source along the source trajectory and also directs the detector along a corollary trajectory. Alternatively, the code directs the rotation of the object to generate a similar relative displacement to the source and detector. Intensity values from the detector are communicated to computer-readable memory, where they are stored in digital form. Additional software code processes the intensity values in accordance with the algorithms described above to obtain the ultimate, reconstructed, three-dimensional image of the object.

Further, the above technique can be used with a wide selection of source orbits as well as variable source-detector configurations.

The new procedure allows simple and systematic approach to cone-beam tomographic reconstructions in general. A number of different source-detector configurations and orientations, as well as a large family of scanning orbits satisfying the so-called data sufficiency condition can be successfully treated in a unified mathematical framework with greater ease, simplicity and improved efficiency. The procedure is immediately suited to the cone-beam systems equipped with large area detectors, in which, the scanned object is positioned completely inside the field of view, and there is no data truncation.

Moreover, source orbits disclosed herein offer better sampling performance in the Radon space and consequently better image qualities in the reconstruction. A new family of source orbits disclosed herein is the biquardatic source curve. The parameters of the biquadratic source curve can be tuned in accordance with the dimension of the scanned object. Another benefit of using the biquadratic curve is that it has at most four intersections with a plane in the three-dimensional space. We are able to give an analytic procedure for deciding the number of intersections between a specified source orbit and an arbitrary plane in the three-dimensional space; the result is used to determine the weights of each plane passing by a particular source point along the source orbit.

BRIEF DESCRIPTION OF THE DRAWINGS

FIG. 1 illustrates a typical cone-beam imaging system with a radiation source and a 2D area detector rotating around the object being scanned.

FIG. 2 provides a schematic illustration of a cone-beam imaging apparatus.

Figure 3:
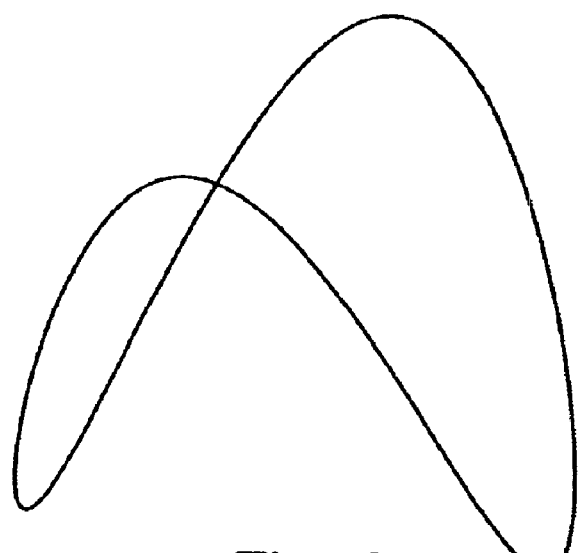
FIG. 3 illustrates a biquadratic source orbit.

FIG. 3 illustrates a biquadratic source orbit.

FIG. 4 provides a visualization of the convexification of the biquadratic source orbit.

Figure 5:
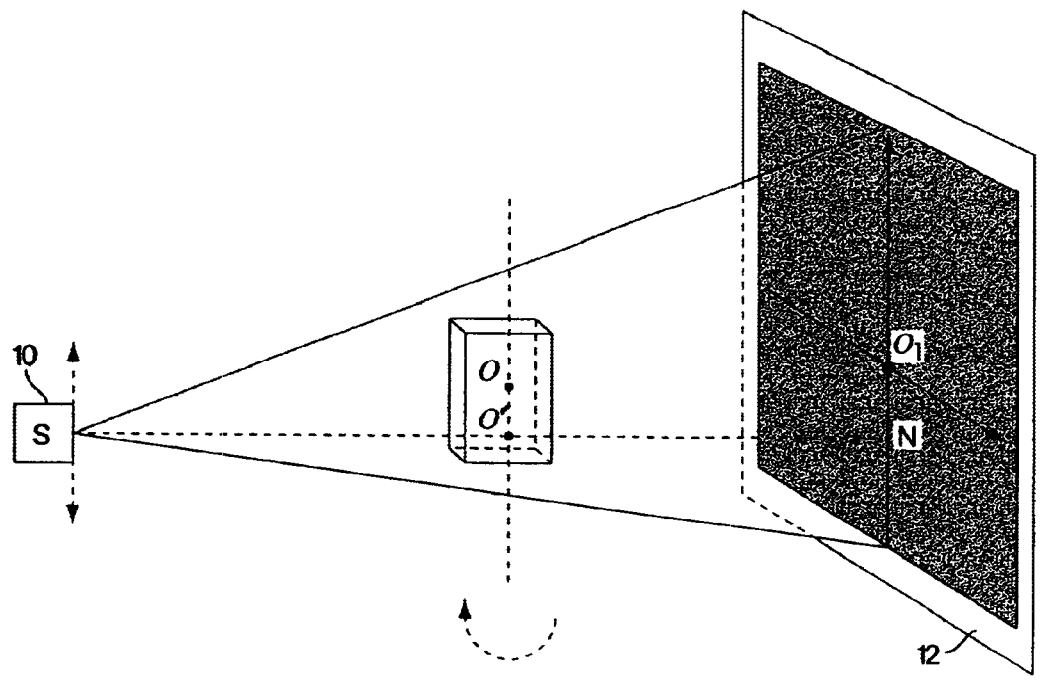
FIG. 5 is an illustration of the detector orientation.

FIG. 5 is an illustration of the detector orientation.

Figure 6:
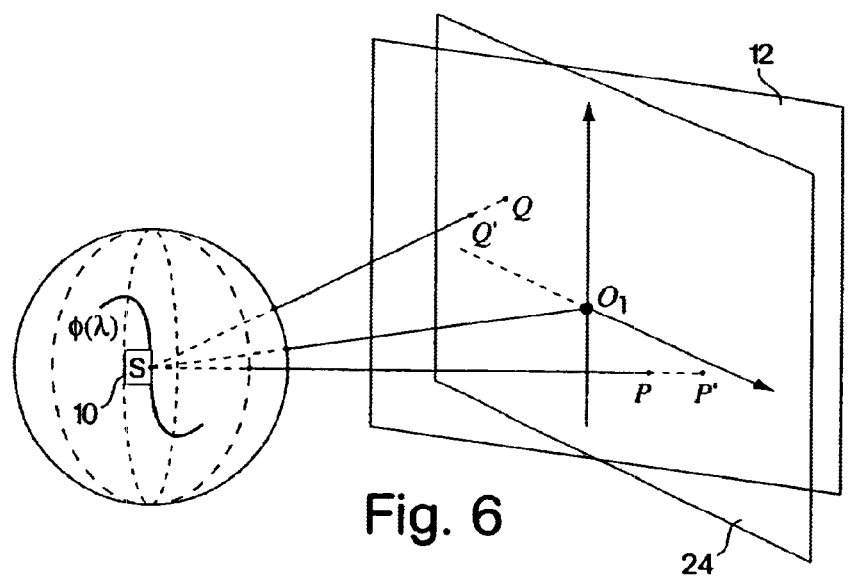
FIG. 6 illustrates the projection of rays from the radiation source onto the detector surface, where there is a one-to-one correspondence between image pixels on the standard image plane and detector elements on the detector surface.

FIG. 6 illustrates the projection of rays from the radiation source onto the detector surface, where there is a one-to-one correspondence between image pixels on the standard image plane and detector elements on the detector surface.

Figure 7:
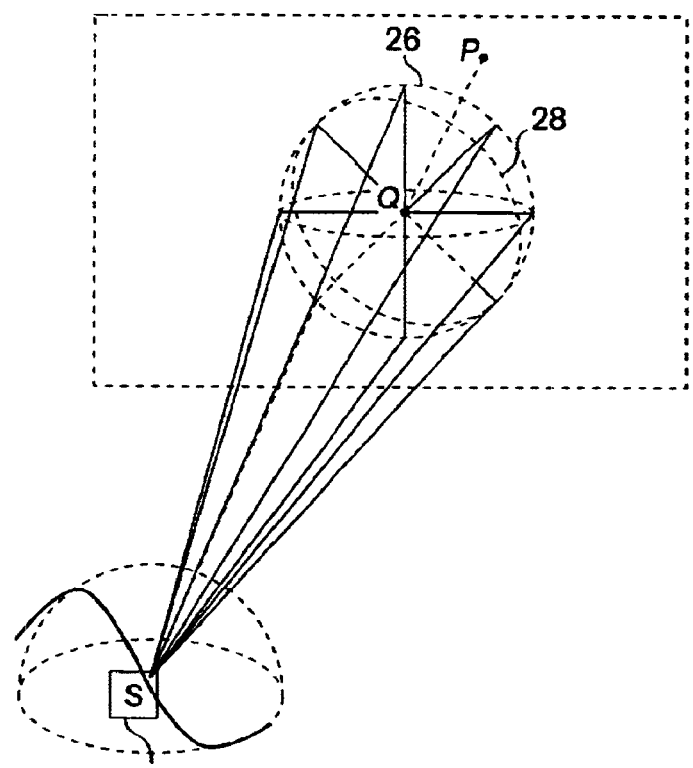
FIG. 7 illustrates a bundle of Radon planes intersecting at a projection line.

FIG. 7 illustrates a bundle of Radon planes intersecting at a projection line.

FIG. 8 illustrates the rigid rotation of the backprojection orientations from projection to projection.

Figure 9:
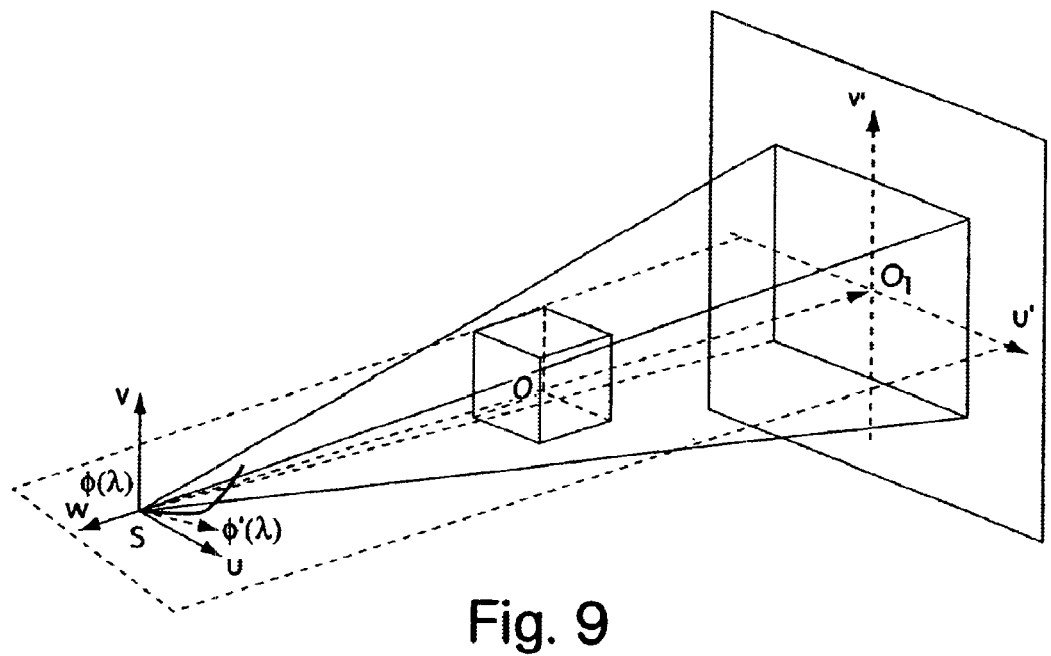
FIG. 9 provides a conceptual image of the moving basis of a first embodiment.

FIG. 9 provides a conceptual image of the moving basis of a first embodiment.

FIG. 10 provides a conceptual image of the moving basis for a second embodiment.

FIG. 11 provides a conceptual image of a Radon plane intersecting the image plane.

FIG. 12 illustrates how the cone-beam slice angle links the global coordinates in the Radon space and the local coordinates on the image plane.

Figure 13:
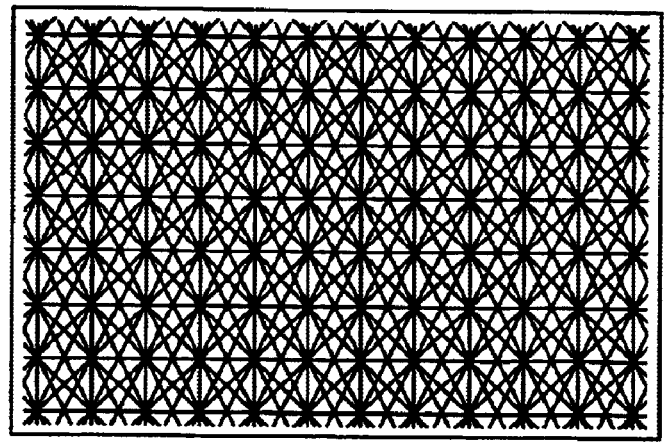
FIG. 13 provides a visualization of processed lines on the standard image plane having rational slopes.

FIG. 13 provides a visualization of processed lines on the standard image plane having rational slopes.

Figure 14:
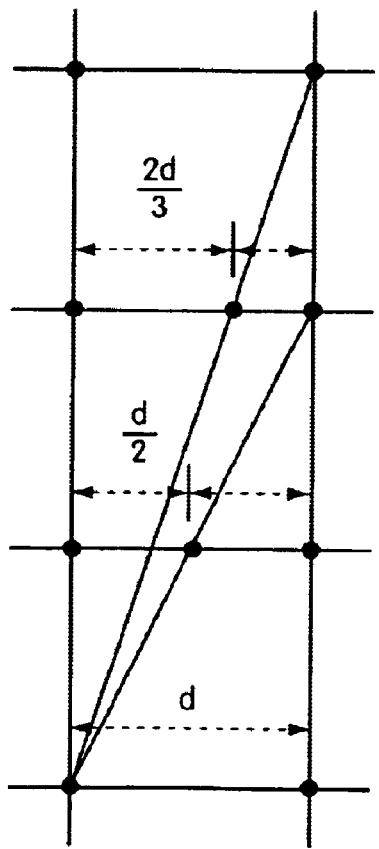
FIG. 14 illustrates an interpolation scheme.

FIG. 14 illustrates an interpolation scheme.

Figure 15:
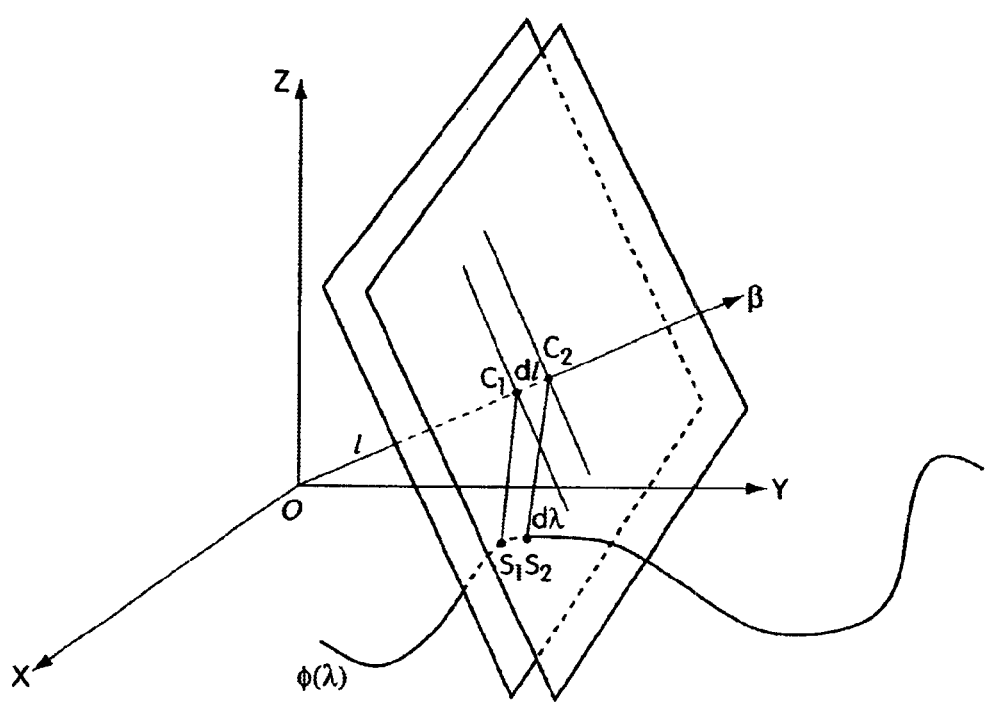
FIG. 15 provides a conceptual image of parallel planes from two consecutive projections.

FIG. 15 provides a conceptual image of parallel planes from two consecutive projections.

FIG. 16 offers a visualization of how a local basis of a line on the image plane is determined by the global coordinates of a Radon plane as well as a moving basis.

FIG. 17 provides a visualization of sampled planes passing by the same projection line meeting the image plane at a set of rational lines.

Figure 18:
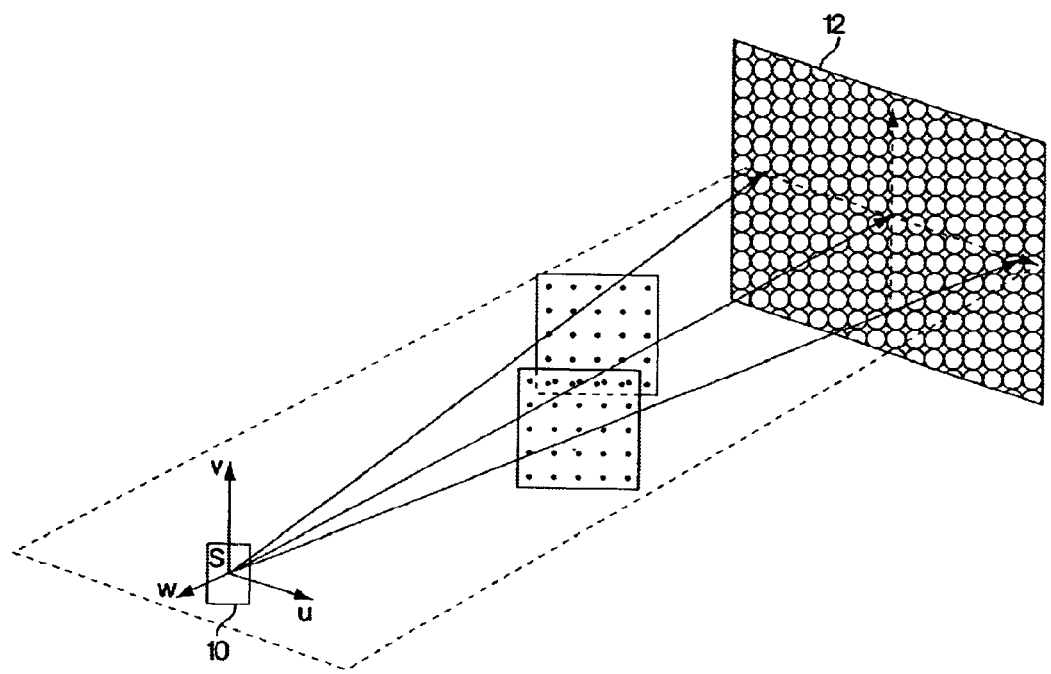
FIG. 18 provides a conceptual image of sampling characteristics of a Cartesian grid that are not aligned with that of the local projection rays.

FIG. 18 provides a conceptual image of sampling characteristics of a Cartesian grid that are not aligned with that of the local projection rays.

The foregoing will be more apparent from the following, more-particular description. In the drawings, like reference characters refer to the same or similar parts throughout the different views. The drawings are not necessarily to scale, emphasis instead being placed upon illustrating particular principles, discussed below.

DETAILED DESCRIPTION

FIG. 2 illustrates a suitable apparatus for generating, detecting a plurality of X-ray cone-beam projections as well as recovering the three-dimensional attenuation map inside the object being scanned from the collected cone-beam projection measurement. Specifically, the physical hardware of a cone-beam imaging system comprises a radiation source 10 with a cone-beam collimator, a two-dimensional area detector 12 that receives the attenuated rays emitting from a point source and passing by the object, two motors 14 and 16, which are accountable for the relative movement between the source-detector system and the object, an analog-to-digital converter 40 that converts the detected cone-beam signals by the area detector into a digital format that enters the computer system 22 as input, and the computer system 22, which stores, processes the converted cone-beam data to reconstruct the attenuation distribution inside the object. The output of the reconstruction is a three-dimensional array that can be recorded in a readable media and displayed by an imaging or graphical display engine.

More specifically, the radiation source and the two-dimensional detector are placed on opposed sides of the object. A cone-beam projection comprises a plurality of projection rays connecting the radiation source and a plurality of detector elements on the detector surface. The plurality of projection rays thus form a cone with the focal point at the source point. The relative position of the source and detector are fixed during the scanning process. Whereas, the relative position of the source-detector pair and the object is controlled by the motors attached to the object support 24 and the source-detector support 26. Various mechanism for rotating the radiation source and the detector around the object are known in the art. For example, the object can be secured on a rotational turntable driven by a motor and the source and detector can be mounted on a pair of parallel slides whose synchronized translation is under the control of another motor. Alternatively, as in a medical CT scan, the radiation source and the detector can be mounted on a cylindrical gantry that rotates, and the object undergoes a simultaneous translation at a constant speed in the direction orthogonal to the rotational gantry. In both cases, the radiation source and the detector seem to travel along a smooth space curve while remaining at a fixed position relative to one another. This curve followed by the radiation source relative to the object being scanned is called the source orbit or the scan path.

Furthermore, the motors are driven by a controller board 18 which is capable of receiving the signals from a computer 16 and generating the commands that set the motors into a prescribed, synchronized rotation and translation. The output of the controller is amplified by the amplifier 20 so that the motor gets the required power for the motion. The imaging display engine 32 is capable of displaying two-dimensional images of the reconstructed attenuation map on an arbitrary cross-section, or processing the reconstructed three-dimensional array using a rendering algorithm that yields a three-dimensional anatomical representation of the object that can be viewed from various angles on a computer screen.

A basic setup for the cone-beam imaging apparatus is to establish the source orbit. Assume that the source orbit is parameterized by $\Phi(\lambda)=(\phi_1(\lambda), \phi_2(\lambda), \phi_3(\lambda))$, with $\lambda \in \Lambda$ being the parameter. Assume also that the source orbit resides outside the convex support of the object, denoted by $\Omega$. A preferred source orbit not only would satisfy the data sufficiency condition, but also would produce considerably even-sampled Radon space, which is defined as the space of all the planes passing by the object.

The data sufficiency condition is imposed to ensure that the collected cone-beam data, after an integral transform, can fill the entire Radon space. A source orbit that satisfies this condition is called a complete source orbit or a complete scan path.

To sample the Radon space uniformly means to produce relatively even-sampled backprojection sphere everywhere in the object space. The second goal is much more difficult to achieve. The size and the shape of the inspected object are important factors in selecting the source orbit; e.g., the optimal source orbit for round and elongated objects shall be different because they exhibit different kind of symmetries. Besides, the separation distance between the X-ray spot and the detector plane as well as the size of the area detector are also important constraints to be considered and accordingly to be compromised when choosing a suitable source orbit.

In one embodiment, the source orbit is controlled by mechanically independent rotational and linear motion. Assume that the rotational axis passes through the center of the object, which is shown in FIG. 2 as a vertical line. The first and second component of the source orbit is therefore on a circle, e.g., $\phi_1(\lambda)=R\cos(\lambda)$, $\phi_2(\lambda)=R\sin(\lambda)$ with $\lambda \in [0,2\pi]$ and R the distance between the source and the rotational axis (this distance is fixed). We assume that the linear translation of the source in the z-dimension relative to the object has the following parametric form:

$$\phi_3(\lambda) = a^2\cos^2\lambda + b^2\sin^2\lambda - \frac{a^2+b^2}{2}. \quad (5)$$

Without loss of generality, we can assume that a>b. Note that $a^2-b^2$ determines the amplitude of the orbit and the ratio $(a^2-b^2)/R$ affects its elongation (See FIG. 3). The curve thus defined can be considered as the intersection of a cylinder and a paraboloid. They are both quadratic surfaces, so the intersecting curve is called biquadratic.

The number of intersections of a plane with a biquadratic curve is either 0, 1, 2, 3, or 4. Given a plane $L_{l,\beta}$, let OC be the line through the origin and perpendicular to the plane. OC intersects the plane at point $l\beta$. At the intersection $\Phi(\lambda)$, where the plane meets the curve, the following identity holds:

$$\beta \cdot (l\beta - \Phi(\lambda)) = 0. \quad (6)$$

It simplifies to $l=\beta \cdot \Phi(\lambda)$. Hence, $$\beta_1 R\cos\lambda + \beta_2 R\sin\lambda + \beta_3(a^2-b^2)\cos^2\lambda - l - \frac{\beta_3(a^2+b^2)}{2} + \beta_3 b^2 = 0. \quad (7)$$

Where $\beta_1$, $\beta_2$ and $\beta_3$ are the three components of $\beta$. Letting $x=\cos\lambda$ ($x \in [-1, 1]$), produces $$\beta_1 Rx + \beta_2 R\sqrt{(1-x^2)} + \beta_3(a^2-b^2)x^2 - l - \frac{\beta_3(a^2+b^2)}{2} + \beta_3 b^2 = 0. \quad (8)$$

The above equation can be rearranged into a quartic equation (fourth order polynomial equation), for which, analytical solutions exist. Since the solutions are given explicitly, we can check if each real root is within [−1, 1]. If it is, then this root corresponds to an intersection point. One can write a simple program to find the number of intersections using the analytical formula for the roots of the quartic equation.

The biquadratic curve parameterized above is highly symmetric. In addition, its shape can be adjusted by the parameters R, a and b according to the dimension of the given problem so to meet the data sufficiency condition. In order for every plane passing through the object intersects with the source orbit, the object must be inside the convex hull of the source orbit. Let two horizontal planes cut through the source orbit near the bottom and the top of the curve; the eight intersections form a trapezoid as shown in FIG. 4. The object is completely inside the convex hull of the source orbit if the object is entirely inside the trapezoid.

Thus we can derive the condition for the parameterized biquadratic curve $\Phi(\lambda)$ being a complete scan path. Assume that the object center is at the origin. Also assume that it has a square base with width w and height h. Then $$a^2 - b^2 > h \& \sqrt{1-\left(1-\frac{h}{(a^2-b^2)R^2}\right)^2} > w \quad (9)$$

guaranties that $\Phi(\lambda)$ is a complete scan path. The above condition can be met by incorporating either $a^2-b^2$ or $R^2$.

One may use any source orbit that is both a complete scan path and analytic, which means that the curve is infinitely differentiable almost everywhere with exception allowed for a zero measure set. In real life most of the curves we encounter are analytic curves. A more general embodiment may encompass any curve that is everywhere differentiable except at a finite number of points, such as a circular trajectory which is not a complete source orbit but which can generate an approximate reconstruction from the incomplete cone-beam data.

Other than the X-ray source configuration, geometric arrangement of the detector is another important component in a cone-beam imaging system. The development in detector technology provides increasingly high resolution X-ray detectors such as the panel system. In one embodiment, a panel detector is used. Its vertical-axis is aligned to the rotational axis of the source orbit and its horizontal axis is parallel to the projection of the tangent of the source orbit at the specified source position on a horizontal plane (see FIG. 5).

Denote by S the source position. Let N be the point where the perpendicular line from the source to the detector plane meets the detector. Let the distance from the detector to the rotational axis be D, which is fixed. The center of the detector image, denoted by $O_I$, may not coincide with N particularly when the area of the detector needs to be maximumly utilized. O' denotes the intersection of the perpendicular line SN and the rotational axis. Under this detector arrangement, data acquisition geometry has a striking cylindrical symmetry. Alternatively, one can utilize the symmetry about the object center and lay the two-dimensional detector array on a plane perpendicular to the line connecting the source and the origin (as shown in FIG. 2).

In practice, the two-dimensional detector surface may be curved or may not be oriented as we described. However, we can treat the above two configurations as two standard image planes. The pixels on any detector surface can be one-to-one mapped to a chosen standard image plane 24 by a geometric transform (see FIG. 6). Given a point on a real detector, the corresponding pixel on the standard image plane is the intersection of the image plane with the line connecting the source to the point. Before getting into the details of the reconstruction steps, a geometric interpretation of the approach is provided.

Assume that a function $f$ on $R^3$ represents the three-dimensional radiation attenuation inside the object being scanned and $f$ has a finite support $\Omega$. The cone-beam image obtained from a particular point source $\Phi(\lambda)$ measures the half line integrals of attenuation along rays passing through $\Phi(\lambda)$:

$$g(\lambda, \alpha) = \int_0^{+\infty} f(\Phi(\lambda) + t\alpha) dt, \ \alpha \in S^2. \quad (10)$$

We name g the X-ray transform of $f$.

There are two distinguished spaces when we process the cone-beam image data. One is the object space in which the three-dimensional attenuation map of the object is to be evaluated. The other is the Radon space, or called the transform space, which is the space of all the planes in $R^3$. Object space and transform space cohabit in the same physical space but they have separate coordinate systems.

Assume that the object space is a uniformly spaced lattice in Cartesian coordinate, say {O: x, y, z} with origin, O at the center of the object, and the z-axis is aligned with the rotational axis of the source orbit. This coordinate is called the global reference frame.

The coordinates identifying a particular Radon plane in the Radon space are $\beta$, the unit normal vector, and l, the perpendicular distance of the plane to the origin. (l, $\beta$) are the global coordinates of the Radon space. One can visualize the Radon space by attaching to each point, $x \in R^3$, a two-dimensional unit sphere, and the points on $S_x^2$ represent the unit normals of all the planes through x. This is the backprojection sphere discussed earlier. Such a representation of the Radon space is redundant since many planes passing by the object intersect with the source orbit multiple times. In the mean time, this redundant representation is advantageous in the reconstruction context since the differential-backprojection operator in the Radon formula (Eqn. (3)), when evaluated for point x, acts on $R''f$ (l, $\beta$) all or almost all planes passing through x, where l=x·$\beta$, and no other planes. The sphere $S_x^2$ is therefore handy for visualizing the geometric computation at the point x, where the function is to be recovered. In the ultimate reconstruction, however, the redundancy is taken into account and each Radon plane shall be weighted by the number of times it meets with the source orbit, which is the redundancy function.

Next, a cone-beam projection from a point source is examined. The divergent beams consist of a family of fan beam slices on those planes passing by the radiation source and an arbitrary line on the two-dimensional image plane; these planes constitute only a subset of all the planes in the projective Radon space. To be able to describe the geometric constraint raised by each cone-beam projection, a point source, say S, is selected and a projection line that connects the source S to a point P on the image plane. Then, for each point Q lying on SP, the family of planes passing by both S and Q intersect at SP. As a result, the normal directions of this set of planes are perpendicular to the projection line SP and are confined to a great circle on the backprojection sphere 26 surrounding Q (see FIG. 7). We call the great circle 28 the backprojection circle.

As the radiation source is moved around the object, the backprojection circle seems to rotate about Q and changes its orientation while still remaining on the back-projection sphere (see FIG. 8). It is a rigid rotation. As long as the source orbit 30 satisfies the data sufficiency condition, the backprojection circles sweeps out and cover the entire backprojection sphere 26.

The geometric analysis leads to the following decomposed Radon inversion formula which is suited for three-dimensional cone-beam reconstruction:

$$f(x) = -\frac{1}{8\pi^2} \int_\Lambda \left\{ \int_{\beta \in \{x - \Phi(\lambda)\}^\perp, \beta \in S^2} R'' f(\Phi(\lambda) \cdot \beta, \beta) \frac{|\Phi'(\lambda) \cdot \beta|}{M(\lambda, \beta)} d\beta \right\} d\lambda \quad (11)$$

where $\{x - \Phi(\lambda)\}^\perp$ denotes the plane perpendicular to $x - \Phi(\lambda)$ and through the origin. The derivative in $R''f$ acts on its first variable, and $M(\lambda, \beta)$ is the redundancy function depicting the number of times that the plane $L_{\Phi(\lambda) \cdot \beta, \beta}$ intersecting with the source orbit.

Reading from Eqn. (11), there is, at each fixed source position, only one two-dimensional backprojection that needs to be performed along each projection ray. The resulting value is constantly assigned to all the points lying on that ray.

For each cone-beam projection, it is convenient to set up a local coordinate with the origin at the source. In the first embodiment, we construct an orthonormal basis with one of the coordinate axes aligned with the rotational axis (the same as the z-axis in the global reference frame); and the other two axes synchronizing with the rotation of the source-detector pair relative to the object when viewed from a horizontal plane (see FIG. 9):

$$\begin{cases} u = \frac{1}{\sqrt{\phi_1^2(\lambda) + \phi_2^2(\lambda)}} (-\phi_2(\lambda), \phi_1(\lambda), 0) \\ v = (0, 0, 1) \\ w = \frac{1}{\sqrt{\phi_1^2(\lambda) + \phi_2^2(\lambda)}} (\phi_1(\lambda), \phi_2(\lambda), 0) \end{cases} \quad (12)$$

As $\lambda$ ranges in $\Lambda$, such a construction generates a set of 3-by-3 orthonormal matrices $O(\lambda) = (u(\lambda), v(\lambda), w(\lambda))$, which are associated with a set of consecutive rotations. The sequence of orthonormal local bases is called a moving frame basis or simply moving basis with the origin anchored on the source orbit.

The way to construct a moving basis is fairly general and flexible; there are variable choices. Preferably, the moving basis represents a natural geometric relationship within each local projection, so the resulting coordinates are simple and brings ease and efficiency into the coordinate computation. The moving basis is often characterized by a smooth evolution from one frame to the next, which allows the computation to be stream-like, more structured and trackable.

In the second preferred embodiment, we can construct the following orthonormal moving basis $$\begin{cases} w = \frac{\Phi(\lambda)}{|\Phi(\lambda)|} \\ v = \frac{w \times \Phi'(\lambda)}{|w \times \Phi'(\lambda)|} \\ u = v \times w \end{cases} \quad (13)$$

with origin attached to the source orbit (see FIG. 10). In both embodiments, the local axes, u and v, are aligned with the axes on the image planes, denoted by u' and v'.

Returning to Eqn. (11), the reconstruction of a three-dimensional function requires the second-order radial derivative of the Radon transform, $R''f$. This is not directly available from the X-ray transform of divergent beams. The evaluation of $R''f$ is carried out in two phases.

According to Grangeat's Fundamental Relation, one can obtain the first-order radial derivative of the Radon transform from cone-beam projection data. FIG. 11 illustrates a Radon plane $L_{l,\beta}$ intersecting the support of $f$. $P_1 P_2$ is the intersection line between $L_{l,\beta}$ and the image plane. Let P be an arbitrary point on $P_1P_2$. Let $\alpha$ be the angle between $L_{l,\beta}$ and the perpendicular line from the source to the image plane, SN. Note that SN may not pass through the global origin. Let the central ray be the shortest line on $L_{l,\beta}$ from the source S to the intersection line $P_1P_2$, denoted by SC. It is easy to verify that SC is perpendicular to $P_1P_2$.

Because the fan beams restricted on the plane $L_{l,\beta}$ all meet at the source, it is natural to use polar coordinates on this plane, with the origin placed at the X-ray source and the axis aligned with the central ray. Denote by r and θ the radial and angular parameters respectively in this polar coordinates. We reformulate the Fundamental Relation as follows:

$$\frac{\partial Rf(l,\beta)}{\partial l} = -\frac{\partial}{\partial \alpha}\left\{\int \frac{1}{\cos\theta}\int f(r)dr d\theta\right\} \quad (14)$$

Where the double integral is performed on the plane $L_{l,\beta}$.

Note that the inner integral in Eqn. (14), $\int f(r) dr$, for some fixed θ, represents the X-ray transform in polar coordinates on the Radon plane $L_{l,\beta}$; this is a measurement available from the cone-beam image. The double integral is the weighted line integral of the X-ray transform; the weight is the cosine of the angle between a particular ray on the Radon plane with the central ray.

Angle $\alpha$ serves as an intuitive link between the coordinates in the local projection frame and the coordinates in the Radon space. In each local projection frame, we are dealing only with lines (on the image plane) instead of planes. However, each line, say $P_1 P_2$, on the image plane is associated to a plane that passes through the source point and intersects the plane by $P_1 P_2$.

On the image plane, assume that the radial distance of the intersection line $P_1 P_2$ from the image center is s and its normal direction, n, form an angle φ with the u'-axis (see FIG. 12).

If the center of the image $O_l$ is aligned to the perpendicular line from the source to the image plane, SN, then (s,φ) can be expressed as $$\begin{cases} \phi = \arctan\left(\frac{\beta \cdot v}{\beta \cdot u}\right) \\ s = (R+D)\tan\alpha \end{cases} \quad (15)$$

If N is off center on the image plane, the radial distance should be offset by the projection of $NO_l$ onto the unit normal, e.g., n=(cos φ, sin φ), of $P_1 P_2$, whereas the angle φ is preserved. It yields $$\begin{cases} \phi = \arctan\left(\frac{\beta \cdot v}{\beta \cdot u}\right) \\ s = (R+D)\tan\alpha - NO_l \cdot n \end{cases} \quad (16)$$

Eqn. (15)-(16) link the α-coordinate to the s-coordinate. Hence, s is a function of α. The partial derivative with respect to α in Eqn. (14) can then be evaluated through the radial derivative of the weighted line integrals on the image plane by $$\frac{\partial}{\partial \alpha} = (R+D)(1-\tan^2\alpha)\frac{\partial}{\partial s}. \quad (17)$$

The image plane has only discrete samples; in other words, there is no real image lines on a image plane. Then the question is, what is the suitable representation of lines on a discrete grid? A line that is represented by the discrete samples on the image plane is called a virtual image line. Under symmetry consideration, we can generate a set of parallel lines with rational slopes in such a way that there are exactly the same number of lines passing through every image pixel (see FIG. 13). Note that a rational slope means it is a ratio of two integers, which allows the set of virtual lines to pass through as many grid nodes as possible.

The fact that the slopes are rational helps to align the pixels on the image plane, which offers great efficiency since the weighted line integral is calculated only once for all the pixels lying on the same rational line. Besides, data interpolation can be done in a very systematic and symmetric way; data points falling between two adjacent nodes can be linearly interpolated from the grid values with weights determined by the separation distance from each neighboring node (see FIG. 14).

For each rational line, say $P_1 P_2$, on the image plane, there is a corresponding plane passing by the source and intersects the image plane by $P_1 P_2$. The global coordinates of the plane in the Radon space, (l, β), can be estimated by $$\begin{cases} \beta = \frac{SP_1 \times SP_2}{|SP_1 \times SP_2|} \\ l = \Phi(\lambda) \cdot \beta \end{cases} \quad (18)$$

Hence, from the line calculation on the image plane we obtain the first-order radial derivative of the Radon transform on a set of two-dimensional planes. The set of selected rational lines determines a set of planes whose coordinates are given by Eqn. (18).

To evaluate the second-order radial derivative of the Radon transform, we construct a set of planes parallel to the planes selected in estimating the first-order Radon derivatives. Since the planes passing by a single source point are non-parallel, the second-order radial derivative of the Radon transform is not available from one cone-beam projection. This second differentiation shall be carried out over the parallel planes from nearby projection frames (See FIG. 15).

The partial derivative with respect to the radial distance, l, is related to the partial derivative with respect to the source orbit parameter, λ, by $$\frac{\partial}{\partial l} = \frac{1}{\Phi'(\lambda) \cdot \beta}\frac{\partial}{\partial \lambda}. \quad (19)$$

In order to find the set of planes in the next cone-beam projection frame parallel to the set of planes chosen by the current projection, we can utilize the method of moving frames. Assume $(l_1, \beta)$ is the global coordinate of a Radon plane processed by the current projection, with $l_1 = \Phi(\lambda_1) \cdot \beta$.

In the subsequent projection, the global coordinates of the plane passing by the next source point $\Phi(\lambda_2)$ and parallel to $L_{l_1,\beta}$ is given by $(l_2, \beta)$, with the same unit normal and with $l_2 = \Phi(\lambda_1) \cdot \beta$. Again, we are dealing with lines instead of planes in the local projection frame. If the perpendicular line from the source to the detector passes through the global origin, as in the second embodiment, the radial distance and the angular variable, (s,φ), of the intersection line between the plane $L_{l_2,\beta}$ and the image plane is given by $$\begin{cases} s = (R+D) \cdot \dfrac{l_2}{\sqrt{R^2 - l_2^2}} \\ \phi = \arctan\left(\dfrac{\beta \cdot v}{\beta \cdot u}\right) \end{cases} \quad (20)$$

in which s is obtained by eliminating $\alpha$ from $\sin \alpha = l_2/R$ and $\tan \alpha = s/(R+D)$ (see FIG. 16).

In the first embodiment, the perpendicular line from the source to the image plane does not pass through the global center; as a result, the radial distance of the plane $L_{\Phi(\lambda_2)\cdot\beta, \beta}$ is offset by $OO' \cdot \beta$. Replacing $l_2$ by $l_2 - OO' \cdot \beta$ in Eqn. (20), we obtain the local coordinates of the intersection line from the second cone-beam image associated to the parallel plane.

The second-order Radon derivative can therefore be evaluated by subtracting the first radial derivative of the Radon transform obtained from two consecutive cone-beam images and dividing by $\Phi(\lambda_2)\cdot\beta - \Phi(\lambda_1)\cdot\beta$. This is essentially the first order approximation through a one-step finite difference. Higher order approximation can be achieved by engaging more cone-beam images. It means that a few more images shall be acquired in advance.

The result is weighted by the multiplicity of each plane intersecting with the source orbit. For the quadratic curve family we have given explicit instructions for finding such intersections, as noted above.

So now, for each node on the image plane, we obtained the second-order radial derivative of the Radon transform on a set of planes corresponding to a set of rational lines passing through the same pixel (see FIG. 17).

This discrete data set is then used to approximate the two-dimensional backprojection on the unit circle perpendicular to the projection line from the source to the image node by $$\sum_{j=0}^{N-1} R'' f(\Phi(\lambda) \cdot \beta_j, \beta_j) \frac{|\Phi'(\lambda) \cdot \beta_j|}{M(\Phi(\lambda) \cdot \beta_j, \beta_j)} \Delta \theta_j \quad (21)$$

where $\beta_j$'s are unit normals of the processed planes and $\theta_j$'s are the angular intervals between $\beta_j$'s.

For a given node on the image plane, the projection line connects this node to the source and is constantly valued by the result of the two-dimensional backprojection. The rays emitting from a single source point are projective whereas the object space is represented by a Cartesian grid. As a result, the local and the global coordinates are characterized by different sampling patterns (see FIG. 18). The projection rays are resampled and interpolated to obtain the nodal values on the Cartesian grid. The simplest interpolation scheme is the nearest neighbor method, i.e., finding the closest line for each Cartesian node and assigning the value of its closest neighbor to it. Higher-order approximation can be achieved by involving more neighboring projection lines.

It is clear that the two-dimensional backprojections yield a three-dimensional image. We call the resulting three-dimensional image a local reconstruction because it is reconstructed from a single projection and its adjacent cone-beam projections, which provide only partial information about the object. Each local reconstruction does not discriminate the variations along each projection line.

The above process is repeated until the cone-beam data acquisition is complete. The ultimate three-dimensional reconstruction is the sum of all the intermediate, locally reconstructed images which can be carried out accumulatively and simultaneously with the scanning and reconstruction process. The contributions from all the local reconstructions are equally weighted. The final output is a three-dimensional array that can be displayed on a computer screen using proper computer graphics engine, either in the slice-by-slice two-dimensional format or in the form of a computer-rendered three-dimensional anatomical representation. It can also be kept in a storage-media for future use.

The moving frame reconstruction paradigm outlined herein can be applied to general cone-beam imaging systems with variable scan paths and detector configurations. When applied, minor details may differ, i.e., the choice of a specific moving basis, or using different sampling and interpolation schemes, etc.; the principle that allows accurate and systematic calculation of the second-order radial derivative of the Radon transform via the method of moving frames does not depart.

While this invention has been shown and described with references to particular embodiments thereof, those skilled in the art will understand that various changes in form and details may be made therein without departing from the scope of the invention, which is limited only by the following claims.

What is claimed is:

1. A method for generating a three-dimensional image of a scanned object from a plurality of cone-beam projections passed through the object and attenuated thereby, the method comprising:

a) positioning the source at an initial position on a predetermined scan path;
   b) passing a projection of cone-beam radiation comprising a plurality of projection rays from a common focal point through an object, the cone-beam projection being attenuated by partial absorption in the object;
   c) detecting radiation intensity of the attenuated cone-beam projection on an area detector and obtaining a two-dimensional attenuation image of the cone-beam projection from the detected radiation intensity;
   d) obtaining an intermediate transform function from the two-dimensional attenuation image on a set of planes passing through the focal point;
   e) at least once, repositioning the source on the predetermined scan path and repeating steps (b)-(d);
   f) filtering the intermediate transform functions acquired from consecutive attenuation images at two or more source positions using a moving-frame technique to obtain the second-order radial derivative of the Radon transform;
   g) backprojecting the second-order radial derivative of the Radon transform in a two-dimensional space along each projection ray passing through a source position among the source positions referenced in step (f) to generate an intermediate, locally reconstructed, three-dimensional image with constant values assigned along each projection ray;
   h) repositioning the source on the predetermined scan path and repeating steps (b)-(d) and (f)-(g);
   i) at least once, repeating step (h); and
   j) summing the plurality of intermediate, locally reconstructed, three-dimensional images obtained for the plurality of cone-beam projections to obtain an ultimate, reconstructed, three-dimensional image of the object.

2. The method of claim 1, wherein the intermediate transform function is the first-order radial derivative of the Radon transform.

3. The method of claim 2, wherein each two-dimensional attenuation image is obtained as a discrete two-dimensional data set with an area detector comprising a plurality of detector elements, and wherein the step of obtaining the first-order radial derivative of the Radon transform includes:
   i) if the area detector does not coincide with the standard image plane:
      a) mapping the coordinates of the detector elements to the coordinates of a set of points on a standard image plane under a projective coordinate transform; and
      b) interpolating the two-dimensional data set to obtain attenuation values on a regular grid on the standard image plane;
   ii) interpolating data points lying between grid nodes along a set of virtual image lines;
   iii) calculating a weighted sum of attenuation along each virtual image line with weights determined by the cosine of the angle between (a) a projection ray associated to a image point and (b) a central ray, which is the shortest line from the source to the virtual image line;
   iv) differentiating the weighted sum over a set of parallel virtual image lines to obtain the first-order radial derivative of the Radon transform on a set of corresponding planes passing through the focal point; and
   v) storing the resulting first-order radial derivative of the Radon transform in memory for use in a subsequent phase of reconstruction.

4. The method of claim 3, wherein the virtual image lines pass through a set of grid nodes on the standard image plane, wherein each grid node has the same number of virtual image lines of different slopes passing through it, and wherein the collection of slopes of the intersecting virtual image lines is the same at each grid node.

5. The method of claim 3, wherein the regular grid has square or rectangular elements.

6. The method of claim 1, wherein the two-dimensional backprojection along a projection ray is an integral over all planes passing by that ray, wherein the unit normal vectors of these planes are confined to a great circle on the unit sphere.

7. The method of claim 1, wherein a plurality of cone-beam projections are successively passed through the object, and wherein the step of determining the second-order radial derivative of the Radon transform includes:
   i) determining the global coordinates, represented by the unit normal and radial distance, of a set of corresponding planes that pass through a set of virtual image lines on the standard image plane and through the current focal point;
   ii) obtaining the first-order radial derivative of the Radon transform on a set of planes for the next one or more cone-beam projections;
   iii) calculating the local parameters of intersection image lines between the standard image planes in successive cone-beam projections and corresponding planes in successive cone-beam projections parallel to the set of planes passing through the current focal point via a coordinate transformation determined by a moving-frame technique;
   iv) interpolating the first-order radial derivative of the Radon transform for the planes obtained in part (iii) from the first-order radial derivative of the Radon transform obtained in part (ii); and
   v) obtaining the second-order radial derivative of the Radon transform by differentiating, which can be approximated by a finite difference, the first-order radial derivative of the Radon transform over the parallel planes from consecutive cone-beam projections.

8. The method of claim 1, wherein the step of backprojecting the second-order radial derivative includes:
   for each projection ray associated with a node on the image plane, calculating a weighted sum of the second-order radial derivative of the Radon transform over a set of planes passing through the projection ray with weights determined by (a) the number of intersections of each plane with the scan path, (b) the absolute value of the dot product between the tangent vector of the scan path at the current source position and the unit normal vector of the plane, and (c) the angular interval between two adjacent planes;
   multiplying the weighted sum by the incremental value of the source orbit parameter, $\lambda$, from the current source position to a next source position;
   assigning the resulting value to points lying on the projection ray; and
   resampling and interpolating the projection rays so that each node on a three-dimensional Cartesian grid representing the object is positioned on one of the rays and is assigned a value to produce a three-dimensional, locally reconstructed image.

9. The method of claim 1, wherein the source is displaced along a complete scan path relative to the object, wherein the scan path intersects with almost all planes passing by the object and the scan path is everywhere differentiable, with exception allowed for a zero measure set, and the cone-beam is generated and passed through the object at a plurality of locations on the complete scan path.

10. The method of claim 9, wherein the scan path is a biquadratic curve.

11. The method of claim 1, wherein the radiation is X-ray radiation.

12. The method of claim 1, wherein the cone-beam projections are detected with an area detector on an opposite side of the object from the radiation source.

13. The method of claim 1, wherein the area detector has a first axis parallel with the rotational axis and a second axis parallel with the projection of the tangent line of the scan path at a current source position onto a plane perpendicular to the rotational axis.

14. The method of claim 1, wherein the detector is placed orthogonal to a line connecting the source to a fixed point residing in the object, and an axis of the detector is aligned with the projection of the tangent of the scan path at a current source position onto the detector.

15. The method of claim 1, wherein the moving frame technique involves the generation of a set of orthonormal bases with the origin of each orthonormal basis positioned at a focal point such that each time the source is repositioned to generate a new focal point and the two-dimensional attenuation image is obtained, the orthonormal basis has a new origin, wherein the moving frame technique enables locating a set of parallel planes from consecutive cone-beam projections and enables the second-order radial derivative of the Radon transforms to be evaluated by filtering over the set of parallel planes from consecutive cone-beam projections.

16. The method of claim 15, wherein the moving frame technique enables location of the planes in the next cone-beam projection parallel to the set of planes in the current projection via a set of coordinate transforms, the method further comprising:
   i) for each selected line on the current standard image plane, finding global coordinates, which can be expressed as l and $\beta$, in the Radon space of a corresponding plane passing through the focal point and intersecting the standard image plane at the selected line;

ii) finding global coordinates, which can be expressed as l and β, of planes passing through the next focal point and parallel to the planes obtained in part (i), wherein two parallel planes have the same unit normal but different radial distances from the global origin;

iii) finding local coordinates, which can be expressed as polar coordinates, s and φ, on the standard image plane, of intersection lines between the planes obtained in part (ii) and the standard image plane of the next cone-beam projection.

17. A computer system for generating a reconstruction of cone-beam radiation attenuation in an object, the computer system comprising:

means for obtaining an intermediate transform function on a set of planes from a signal representing the amount of radiation transmitted through the object;

means for calculating the second-order radial derivative of the Radon transform by filtering the intermediate transform function from consecutive two-dimensional cone-beam measurements over a set of parallel planes using a moving-frame technique;

means for backprojecting the second-order radial derivative of the Radon transform to generate an intermediate, locally reconstructed, three-dimensional image with constant values assigned along each projection ray; and an accumulation buffer to sum the plurality of intermediate, locally reconstructed, three-dimensional images obtained for the cone-beam projections to obtain an ultimate, reconstructed, three-dimensional image of the object.

18. A computer-readable storage medium storing computer-executable software for generating a reconstruction of cone-beam radiation attenuation in an object, the software comprising:

code for obtaining an intermediate transform function on a set of planes from a signal representing the amount of radiation transmitted through the object;

code for calculating the second-order radial derivative of a Radon transform by filtering the intermediate transform function over a set of parallel planes using a moving-frame technique;

code for backprojecting the second-order radial derivative of the Radon transform to generate an intermediate, partially reconstructed, three-dimensional image with constant values assigned along each projection ray; and code for summing the plurality of intermediate, locally reconstructed, three-dimensional images obtained for the cone-beam projections to obtain an ultimate, reconstructed, three-dimensional image of the object.

19. A cone-beam tomography apparatus comprising a computer-readable storage medium storing computer-executable software for generating a reconstruction of cone-beam radiation attenuation in an object, the software comprising:

code for obtaining an intermediate transform function on a set of planes from a signal representing the amount of radiation transmitted through the object;

code for determining the second-order radial derivative of the Radon transform by filtering the intermediate transform function over a set of parallel planes using a moving-frame technique;

code for backprojecting the second-order radial derivative of the Radon transform to generate an intermediate, locally reconstructed, three-dimensional image with constant values assigned along each projection ray; and code for summing the plurality of intermediate, locally reconstructed, three-dimensional images obtained for the cone-beam projections to obtain an ultimate, reconstructed, three-dimensional image of the object.

20. The cone-beam tomography apparatus of claim 19, further comprising a radiation source, a radiation detector, a support for the radiation source and detector, a support for an object to be scanned by radiation from the radiation source, and one or more linear and rotary motors for providing relative movement between the source and detector and the object.

21. The cone-beam tomography apparatus of claim 20, wherein the software further comprises code for displacing the source and detector relative to the support for the object to provide a biquadratic scan path for radiation transmitted from the source, through the object positioned by the support, and to the detector.

22. A cone-beam tomography apparatus for generating a reconstruction of cone-beam radiation attenuation in an object, the apparatus comprising means for obtaining an intermediate transform function on a set of planes from a signal representing the amount of radiation transmitted through the object;

means for determining the second-order radial derivative of the Radon transform by filtering the intermediate transform function over a set of parallel planes using a moving-frame technique;

means for backprojecting the second-order radial derivative of the Radon transform to generate an intermediate, locally reconstructed, three-dimensional image with constant values assigned along each projection ray; and means for summing the plurality of intermediate, locally reconstructed, three-dimensional images obtained for the cone-beam projections to obtain an ultimate, reconstructed, three-dimensional image of the object.

* * * * *